US010357381B2

(12) United States Patent
Kuiken et al.

(10) Patent No.: US 10,357,381 B2
(45) Date of Patent: Jul. 23, 2019

(54) POWERED AND PASSIVE ASSISTIVE DEVICE AND RELATED METHODS

(71) Applicant: Rehabilitation Institute of Chicago, Chicago, IL (US)

(72) Inventors: Todd Kuiken, Oak Park, IL (US); James Lipsey, Oak Park, IL (US); Tommaso Lenzi, Chicago, IL (US); Marco Cempini, Chicago, IL (US)

(73) Assignee: Rehabilitation Instititute of Chicago, Chicago, IL (US)

( * ) Notice: Subject to any disclaimer, the term of this patent is extended or adjusted under 35 U.S.C. 154(b) by 0 days.

(21) Appl. No.: 14/962,982

(22) Filed: Dec. 8, 2015

(65) Prior Publication Data

US 2016/0158029 A1    Jun. 9, 2016

Related U.S. Application Data

(60) Provisional application No. 62/088,849, filed on Dec. 8, 2014.

(51) Int. Cl.
*A61F 2/50* (2006.01)
*A61F 2/60* (2006.01)
(Continued)

(52) U.S. Cl.
CPC .................. *A61F 2/60* (2013.01); *A61F 2/54* (2013.01); *A61F 2/64* (2013.01); *A61F 2/642* (2013.01); *A61F 2/68* (2013.01); *A61F 2/70* (2013.01); *A61F 5/0123* (2013.01); *A61H 1/024* (2013.01); *A61H 3/00* (2013.01); *A61F 2/6607* (2013.01); *A61F 2002/5006* (2013.01); *A61F 2002/5016* (2013.01); *A61F 2002/5072* (2013.01); *A61F 2002/5087* (2013.01);
(Continued)

(58) Field of Classification Search
CPC ..................................... A61F 2/68; A61F 2/70
See application file for complete search history.

(56) References Cited

U.S. PATENT DOCUMENTS 2,316,558 A   4/1943 Camilli
2,568,051 A   9/1951 Catranis
(Continued)

FOREIGN PATENT DOCUMENTS

CH        543277 A     10/1973
CN      2043873 U      9/1989
(Continued)

OTHER PUBLICATIONS

Three-page printout from http://www.eksobionics.com/ekso website regarding "Ekso Bionics—Exoskeleton, wearable robot for people with paralysis from SCI or stroke," accessed on Feb. 15, 2016.
(Continued)

*Primary Examiner* — Jacqueline Woznicki
(74) *Attorney, Agent, or Firm* — McAndrews, Held & Malloy, Ltd.

(57) ABSTRACT

Systems and methods for assistive devices for replacing or augmenting the limb of an individual, such devices comprising a joint and a powered system; the powered system having a first configuration in which the powered system rotates the joint by applying power to the joint, and a second configuration that allows for rotation of the joint without actuation of the powered system.

19 Claims, 29 Drawing Sheets

(51) Int. Cl.

| | |
|---|---|
| *A61F 2/64* | (2006.01) |
| *A61F 2/68* | (2006.01) |
| *A61F 2/70* | (2006.01) |
| *A61F 2/54* | (2006.01) |
| *A61F 5/01* | (2006.01) |
| *A61H 1/02* | (2006.01) |
| *A61H 3/00* | (2006.01) |
| *A61F 2/66* | (2006.01) |
| *A61F 2/76* | (2006.01) |

(52) U.S. Cl.
CPC ............ *A61F 2002/6845* (2013.01); *A61F 2002/6854* (2013.01); *A61F 2002/701* (2013.01); *A61F 2002/704* (2013.01); *A61F 2002/764* (2013.01); *A61F 2002/7625* (2013.01); *A61F 2002/7635* (2013.01); *A61F 2005/0144* (2013.01); *A61F 2005/0148* (2013.01); *A61F 2005/0155* (2013.01); *A61F 2005/0169* (2013.01); *A61H 2201/0165* (2013.01); *A61H 2201/123* (2013.01); *A61H 2201/1238* (2013.01); *A61H 2201/149* (2013.01); *A61H 2201/1445* (2013.01); *A61H 2201/164* (2013.01); *A61H 2201/165* (2013.01); *A61H 2201/1676* (2013.01); *A61H 2201/5058* (2013.01); *A61H 2201/5061* (2013.01); *A61H 2201/5097* (2013.01); *A61H 2230/605* (2013.01)

(56) References Cited

U.S. PATENT DOCUMENTS

| | | | |
|---|---|---|---|
| 2,619,652 A | 12/1952 | Vesper | |
| 2,859,451 A | 11/1958 | Mauch | |
| 3,316,558 A | 5/1967 | Mortensen | |
| 3,417,409 A | 12/1968 | Prahl | |
| 3,823,424 A * | 7/1974 | May ................. | A61F 2/644 623/39 |
| 4,310,932 A * | 1/1982 | Nader .............. | A61F 2/644 623/39 |
| 4,723,539 A * | 2/1988 | Townsend .......... | A61F 5/0123 602/16 |
| 5,020,790 A | 6/1991 | Beard et al. | |
| 5,246,465 A | 9/1993 | Rincoe et al. | |
| 5,545,232 A * | 8/1996 | Van de Veen ...... | A61F 2/644 623/39 |
| 5,800,567 A * | 9/1998 | Cooper ............... | A61F 2/642 623/39 |
| 6,610,101 B2 | 8/2003 | Herr et al. | |
| 6,955,692 B2 | 10/2005 | Grundei | |
| 6,966,882 B2 | 11/2005 | Horst | |
| 7,537,573 B2 | 5/2009 | Horst | |
| RE42,903 E | 11/2011 | Deffenbaugh et al. | |
| 8,048,007 B2 | 11/2011 | Roy | |
| 8,211,042 B2 | 7/2012 | Gilbert et al. | |
| 8,281,680 B2 | 10/2012 | Huang et al. | |
| 8,287,477 B1 | 10/2012 | Herr et al. | |
| 8,435,309 B2 | 5/2013 | Gilbert et al. | |
| 8,500,823 B2 | 8/2013 | Herr et al. | |
| 8,551,184 B1 | 10/2013 | Herr | |
| 8,652,218 B2 | 2/2014 | Goldfarb et al. | |
| 8,679,040 B2 | 3/2014 | Horst | |
| 8,814,949 B2 | 8/2014 | Gramnaes | |
| 8,974,543 B2 | 3/2015 | Balboni et al. | |
| 9,017,419 B1 | 3/2015 | Landry et al. | |
| 9,066,817 B2 | 6/2015 | Gilbert et al. | |
| 2002/0177905 A1* | 11/2002 | Yih ................... | A61F 2/54 623/24 |
| 2004/0049290 A1* | 3/2004 | Bedard .............. | A61F 2/644 623/24 |
| 2004/0111163 A1* | 6/2004 | Bedard .............. | A61F 2/644 623/33 |
| 2004/0181289 A1* | 9/2004 | Bedard .............. | A61F 2/644 623/24 |
| 2006/0173552 A1 | 8/2006 | Roy | |
| 2007/0083272 A1* | 4/2007 | Van De Veen ...... | A61F 2/644 623/39 |
| 2009/0299489 A1 | 12/2009 | Gramnaes | |
| 2010/0023133 A1* | 1/2010 | Fairbanks ............ | A61F 2/64 623/24 |
| 2010/0318006 A1 | 12/2010 | Horst | |
| 2011/0224803 A1 | 9/2011 | Goldfarb et al. | |
| 2012/0316475 A1 | 12/2012 | Bhugra et al. | |
| 2012/0330439 A1 | 12/2012 | Goldfarb et al. | |
| 2013/0023800 A1 | 1/2013 | Bedard et al. | |
| 2013/0204395 A1 | 8/2013 | Gramnaes | |
| 2014/0114438 A1 | 4/2014 | Goldfarb et al. | |
| 2014/0195007 A1 | 7/2014 | Goldfarb et al. | |
| 2015/0018970 A1 | 1/2015 | Gilbert | |

FOREIGN PATENT DOCUMENTS

| | | |
|---|---|---|
| CN | 201356682 Y | 12/2009 |
| CN | 202801868 | 3/2013 |
| CN | 103445891 | 12/2013 |
| GB | 607001 | 8/1948 |
| WO | 2004/017872 A1 | 3/2004 |
| WO | WO2011123951 A1 | 10/2011 |
| WO | 2014/005679 A2 | 1/2014 |
| WO | WO2014032775 A1 | 3/2014 |
| WO | 2014151584 | 9/2014 |

OTHER PUBLICATIONS

Four-page printout from https://web.archive.org/web/20140625073705/http://www.keeogo.com/ website regarding "B-Temia Human augmentation systems, restore and enhance mobility," accessed on Feb. 15, 2016.

Five-page printout from http://rewalk.com/# website "Introducing the: ReWalk Personal 6.0 System," accessed on Feb. 15, 2016.

A. J. Young et al., "Analysis of using EMG and mechanical sensors to enhance intent recognition in powered lower limb prostheses", IOP Publishing, Journal of Neural Engineering 11 (2014) 056021, 12 pp. plus IOP Science cover page.

Rafael Roberto Medina, "Feasibility and Design Study for a Motorized A/K Prosthesis," Thesis for Bachelor of Science at the Massachusetts Institute of Technology, 58 pp.

Ernesto C. Martinez-Villalpando, et al., "Agonist-antagonist active knee prosthesis: A preliminary study in level-ground walking," Journal of Rehabilitation Research & Development, vol. 46, No. 3, 2009, pp. 361-374.

Bram G. A. Lambrecht, "Design of a Hybrid Passive-Active Prosthesis for Above-Knee Amputees," Graduate Division of the University of California, Berkeley, Fall 2008.

Otto Bock Healthcare LP, "World's First Orthotronic System—You'll always remember your first step," Jun. 2012.

Otto Bock Healthcare LP, "The New Orthotronic Mobility Device," Aug. 2013.

Michael F. Eilenberg, et al., "Control of a Powered Ankle-Foot Prosthesis Based on a Neuromuscular Model," IEEE Transactions on Neural Systems and Rehabilitation Engineering, vol. 18, No. 2, Apr. 2010.

Frank Sup, et al., "Preliminary Evaluations of a Self-Contained Anthropomorphic Transfemoral Prosthesis," IEEE/ASME Transations on Mechatronics, vol. 14, No. 6, Dec. 2009.

Frank Sup, et al., "Upslope Waling With a Powered Knee and Anle Prosthesis: Initial Results With an Amputee Subject," IEEE Transactions on Neural Systems and Rehabilitation Engineering, vol. 19, No. 1, Feb. 2011.

Frank Sup, et al., "Design and Control of a Powered Transfemoral Prosthesis," The International Journal of Robotics Research, vol. 27, No. 2, Feb. 2008, pp. 263-273.

Levi J. Hargrove, et al. , "Robotic Leg Control with EMG Decoding in an Amputee with Nerve Transfers," The New England Journal of Medicine, 369;13, Sep. 2013.

(56) References Cited

OTHER PUBLICATIONS

Technology by Ossur, Bionic, Instructions for use Power Knee, 22-page brochure, IFU 0257 EN Rev. 3.

Otto Bock HealthCare GmbH, "Modular Lightweight Knee Joints, The right swing," 2-page brochure.

Jacob Rosen, et al., "A Myosignal-Based Powered Exoskeleton System," IEEE Transation on Systems, Man and Cybernetics—Part A: Systems and Humans, vol. 31, No. 3, May 2001.

Otto Bock Healthcare, LLC, "Ottobock Advanced Orthotics—Stance Control KAFOs and Unilateral Joints," 12-page brochure, Apr. 2013.

Walid Hassani, et al., "Real-Time EMG driven Lower Limb Actuated Orthosis for Assistance as Needed Movement Strategy," LISSI Lab, University Paris Est Creteil (UPEC), France.

Joy Singh Akoijam, "Understanding robotics in rehabilitation," Review Article, Indian Association of Physical Medicine & Rehabilitation, West Bengal Branch, Jul. 21, 2011.

Elliott J. Rouse, et al., "Clutchable Series-Elastic Actuator: Design of a Robotic Knee Prosthesis for Minimum Energy Consumption," MIT Media Lab, Massachusetts Institute of Technology.

Matthieu Duvinage, et al. "Human Walk Modeled by PCPG to Control a Lower Limb Neuroprosthesis by High-Level Commands," LNMB Lab, Universite Libre de Bruxelles, Belgium.

Matthew A. Holgate, et al. "A Novel Control Algorithm for Wearable Robotics using Phase Plane Invariants," 2009 IEEE International Conference on Robotics and Automation, Kobe, Japan, May 12-17, 2009.

Michael R. Tucker, et al. "Design of a Wearable Perturbator for Human Knee Impedance Estimation during Gait," 2013 IEEE International Conference on Rehabilitation Robotics, Seattle, WA, Jun. 24-26, 2013.

Yifan Li, On Improving Control and Efficiency of a Portable Pneumatically Powered Ankle-Foot Orthosis, Dissertation, University of Illinois at Urgana-Champaign, 2013.

Aaron J. Young, et al., "A Training Method for Locomotion Mode Prediction Using Powered Lower Limb Prostheses," DOI: 10.1109/TNSRE.2013.2285101, IEEE Transactions on Neural Systems and Rehabilitation Engineering, 2013.

Aaron J. Young, et al., "Intent Recognition in a Powered Lower Limb Prosthesis Using Time History Information," Annals of Biomedical Engineering, 2013, DOI: 10.1007/s10439-013-0909-0.

hhttps://www.youtube.com/watch?v=Q9zPITLCG9c—Video concerning MOBIS® Otto Bock Mobility System 3R90-92.

https://www.youtube.com/watch?v=s8mNP2cdbiE&feature=youtu.be—"The Parker Indego® Powered Lower Limb Exoskeleton."

PCT International Search Report and Written Opinion dated Mar. 2, 2016 for PCT Patent Application Matter PCT/US2015/64516.

Extended European Search Report Appln No. 15867127.1 dated Jul. 5, 2018 (7 pgs.).

\* cited by examiner

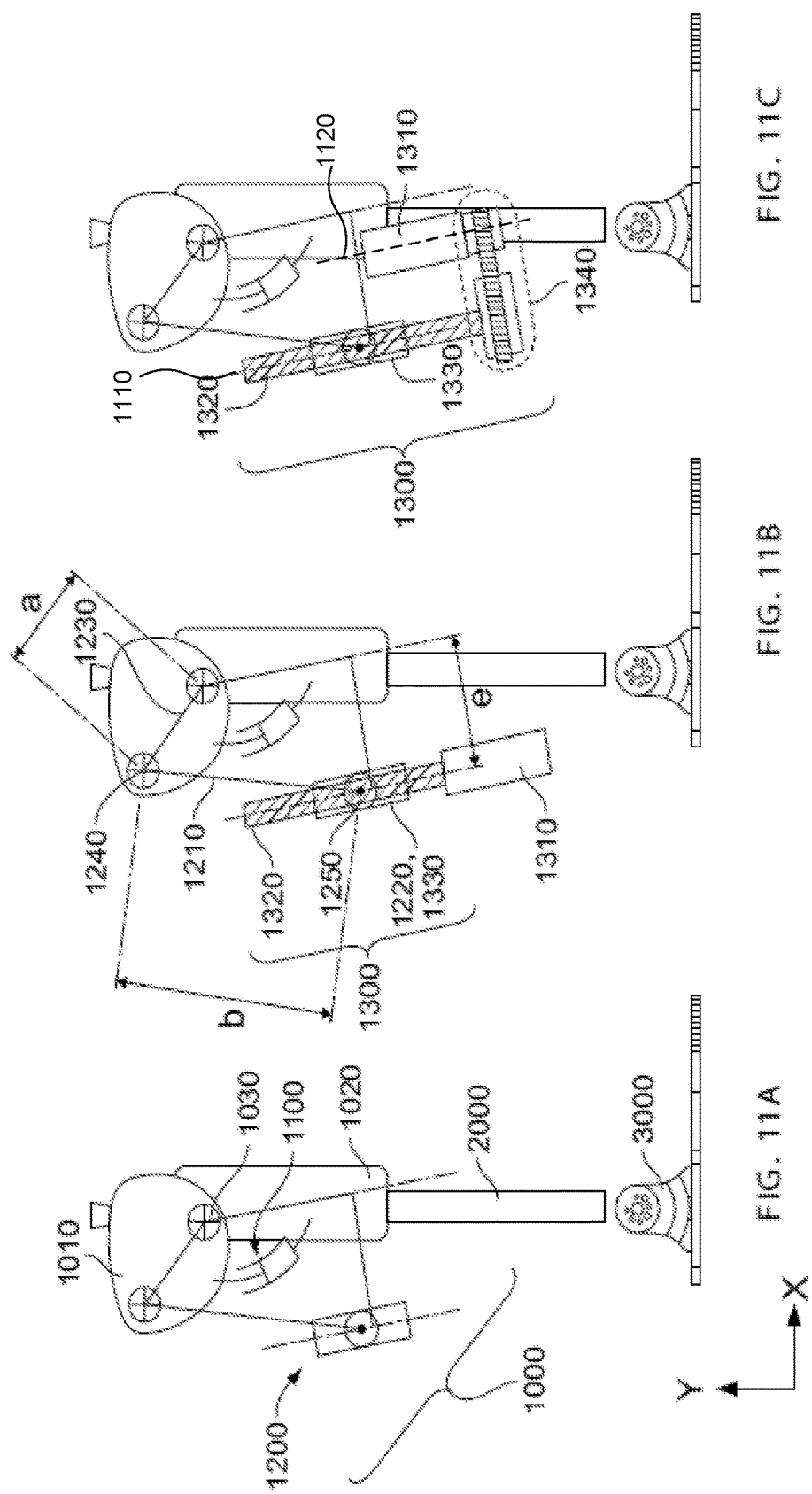

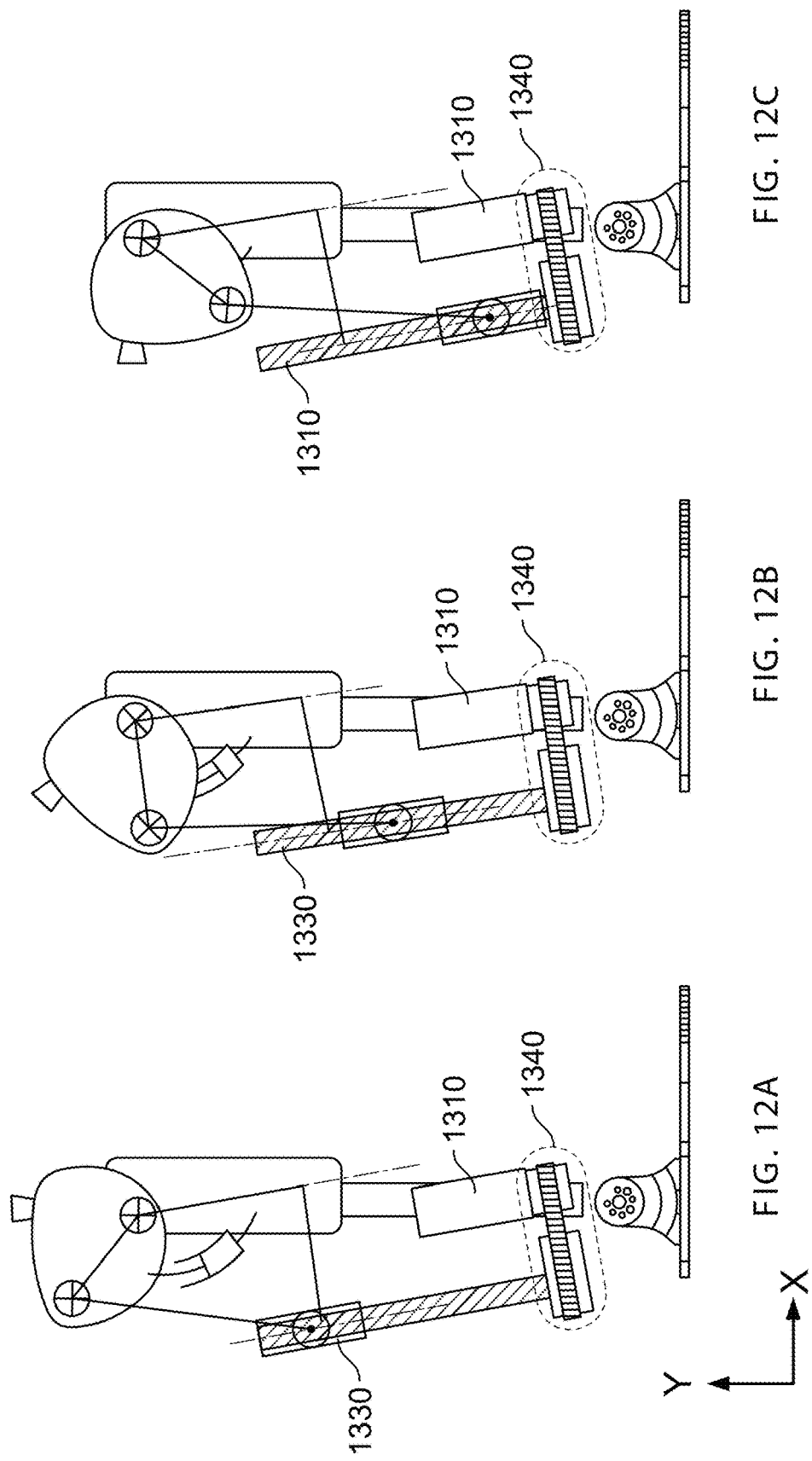

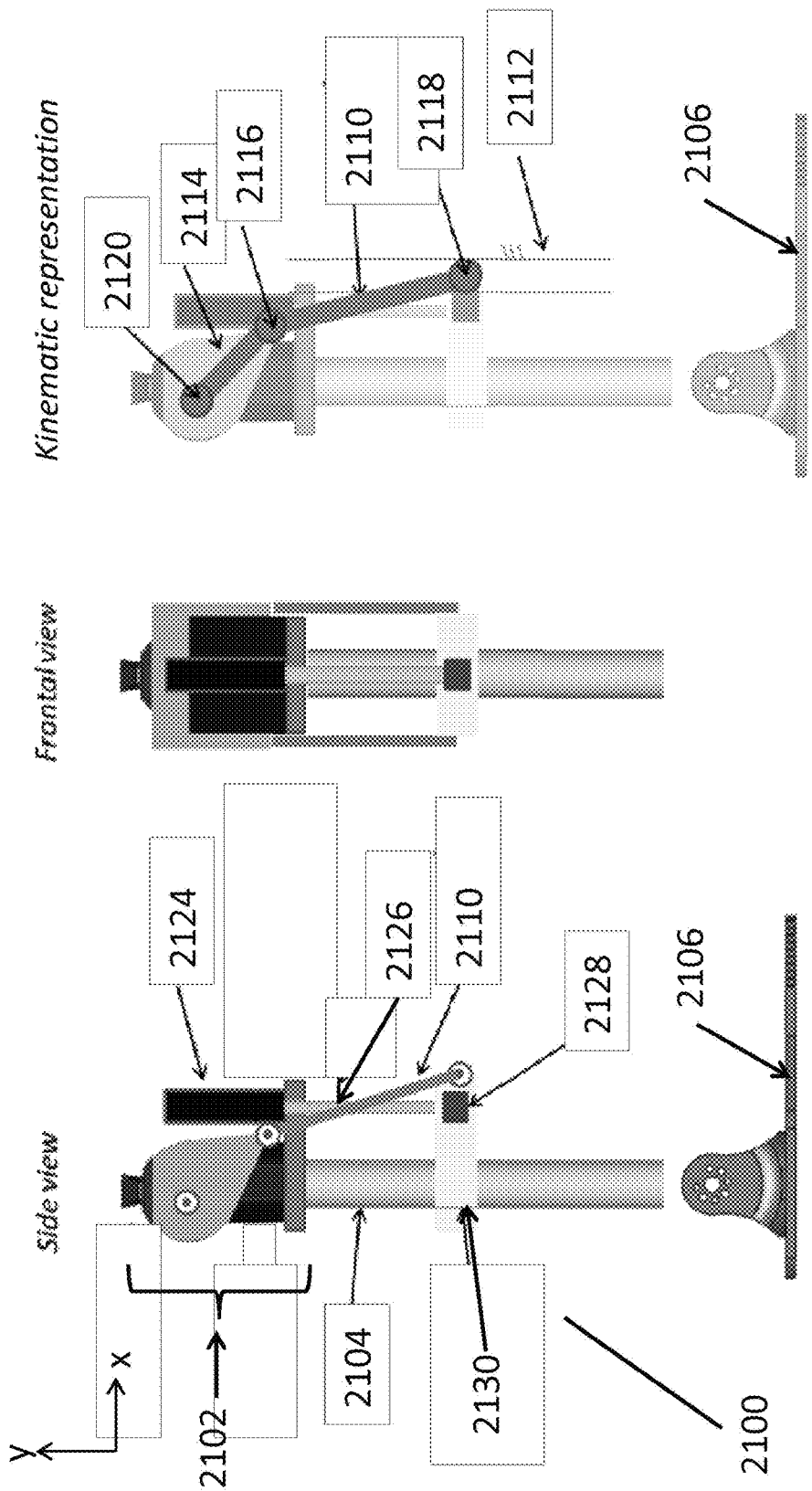

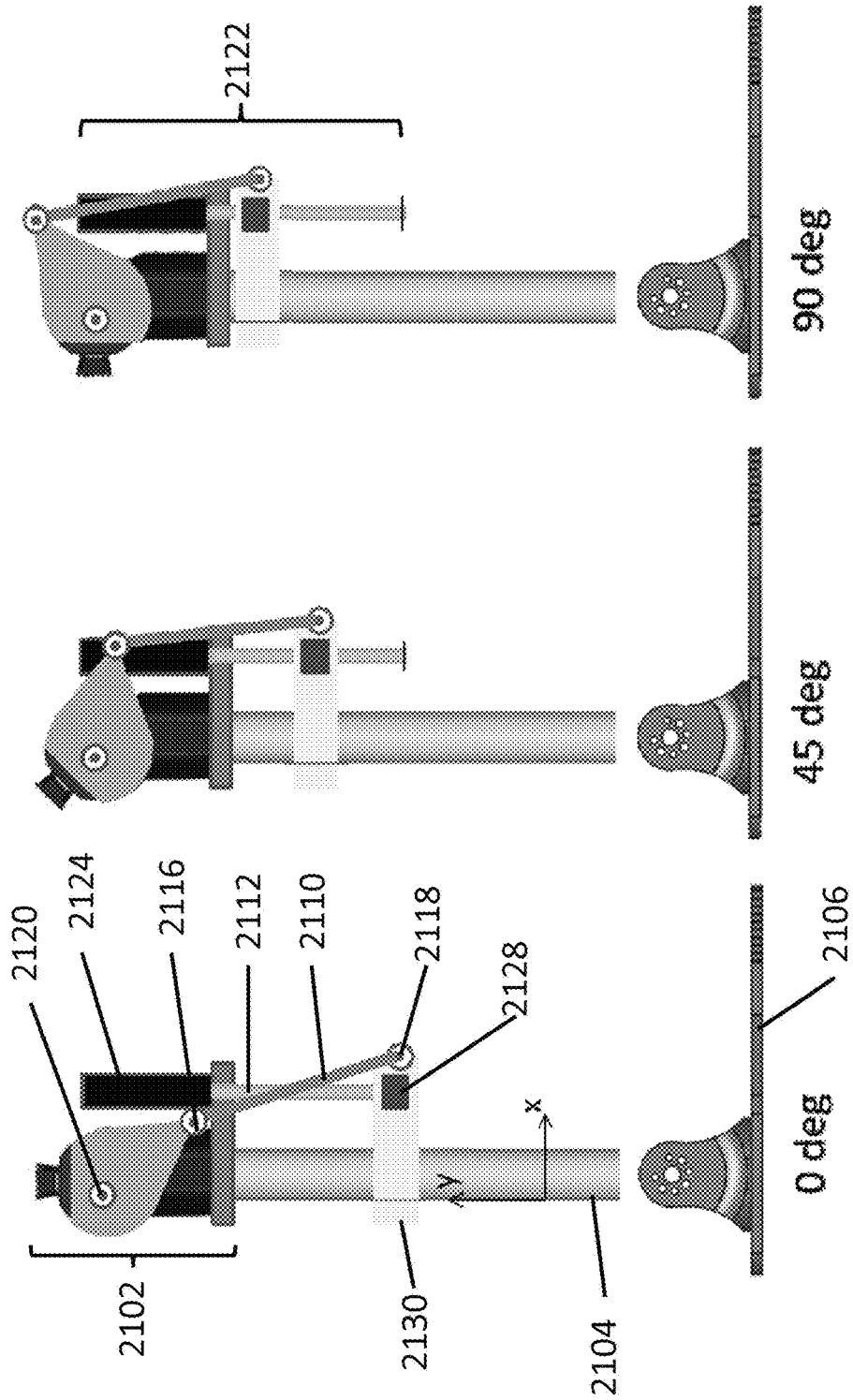

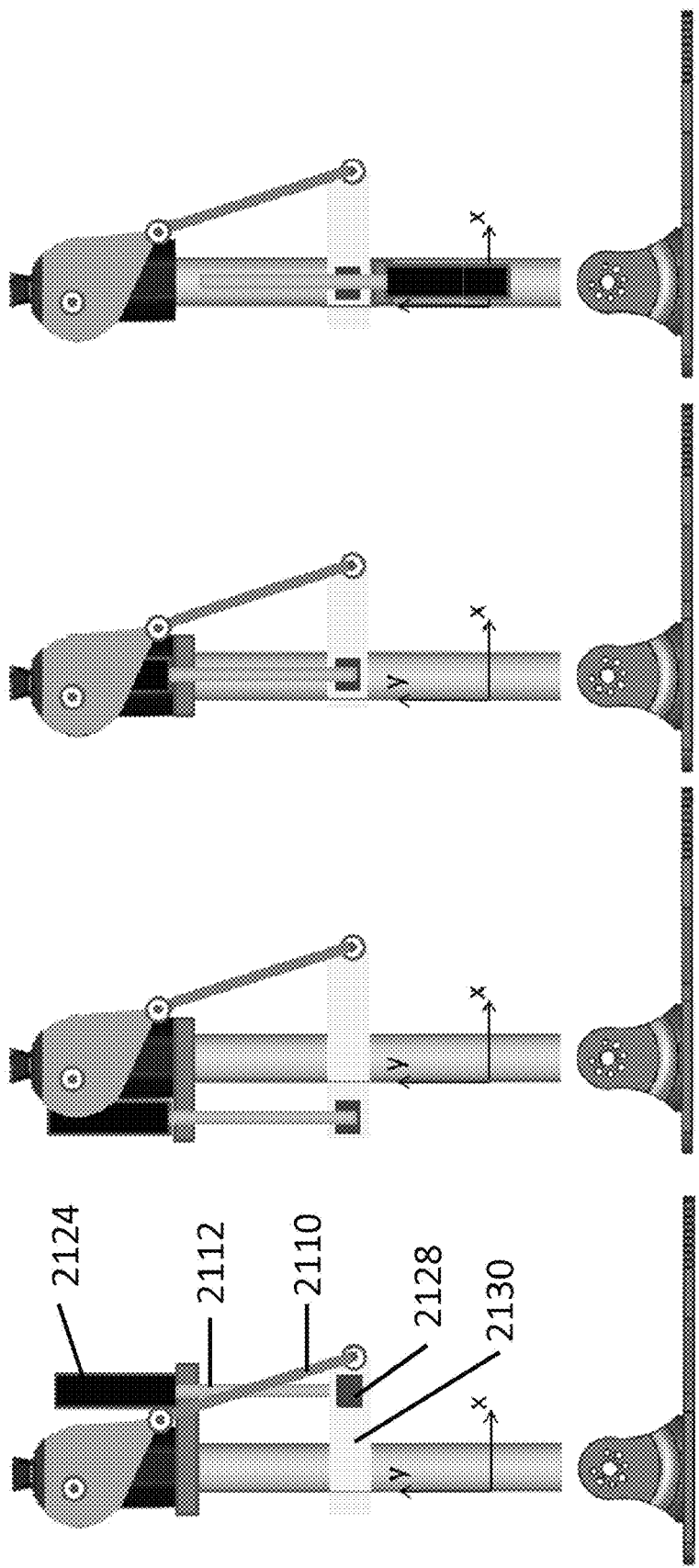

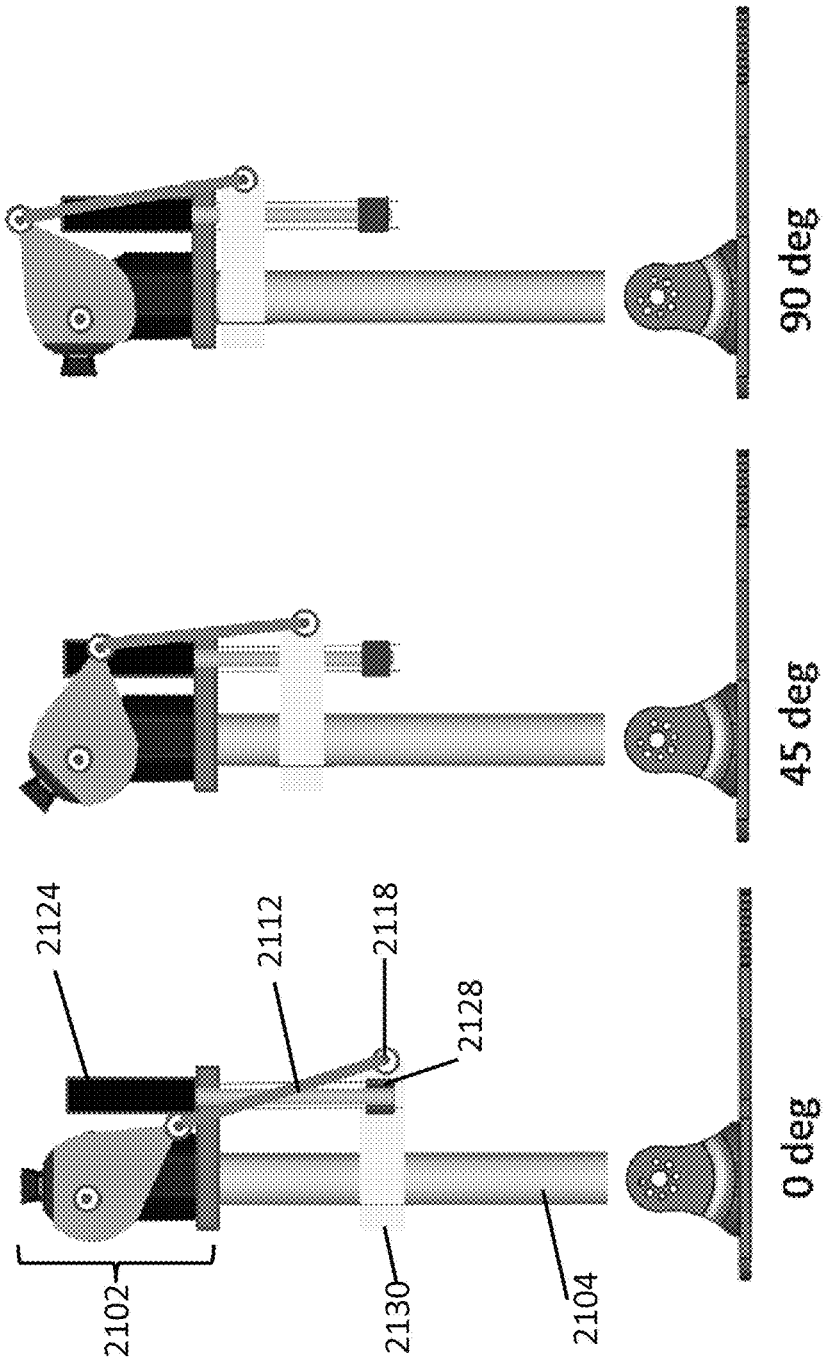

SWITCHING MECHANISM – PRISMATIC JOINT
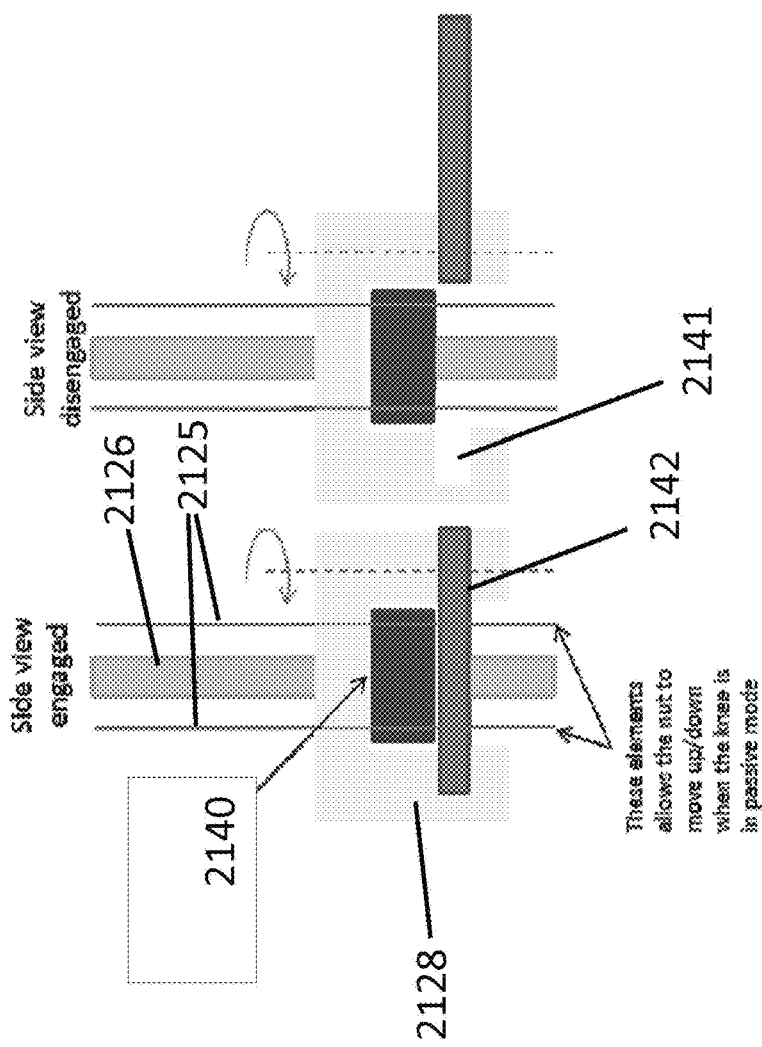
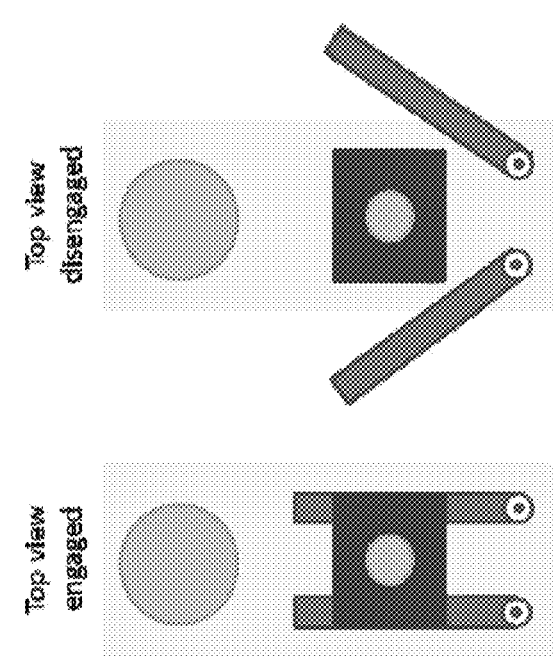
FIG. 23A     FIG. 23B     FIG. 23C     FIG. 23D

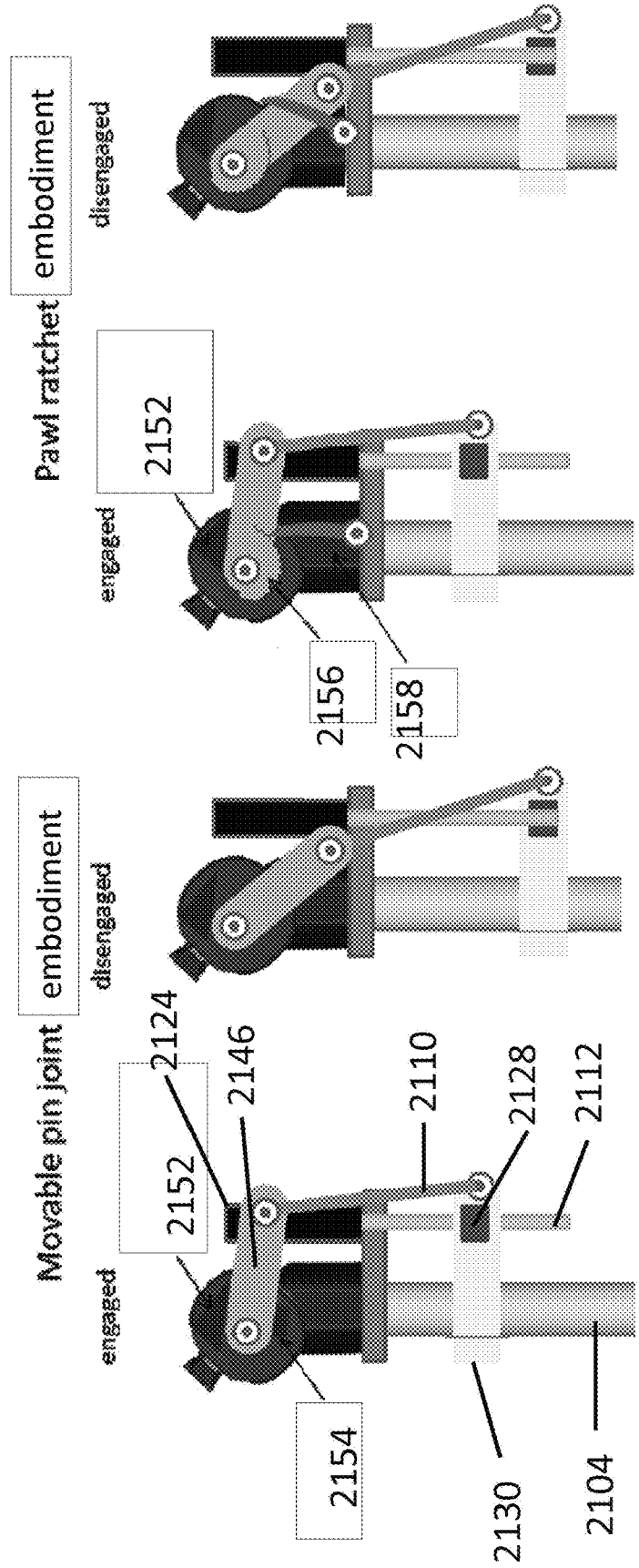

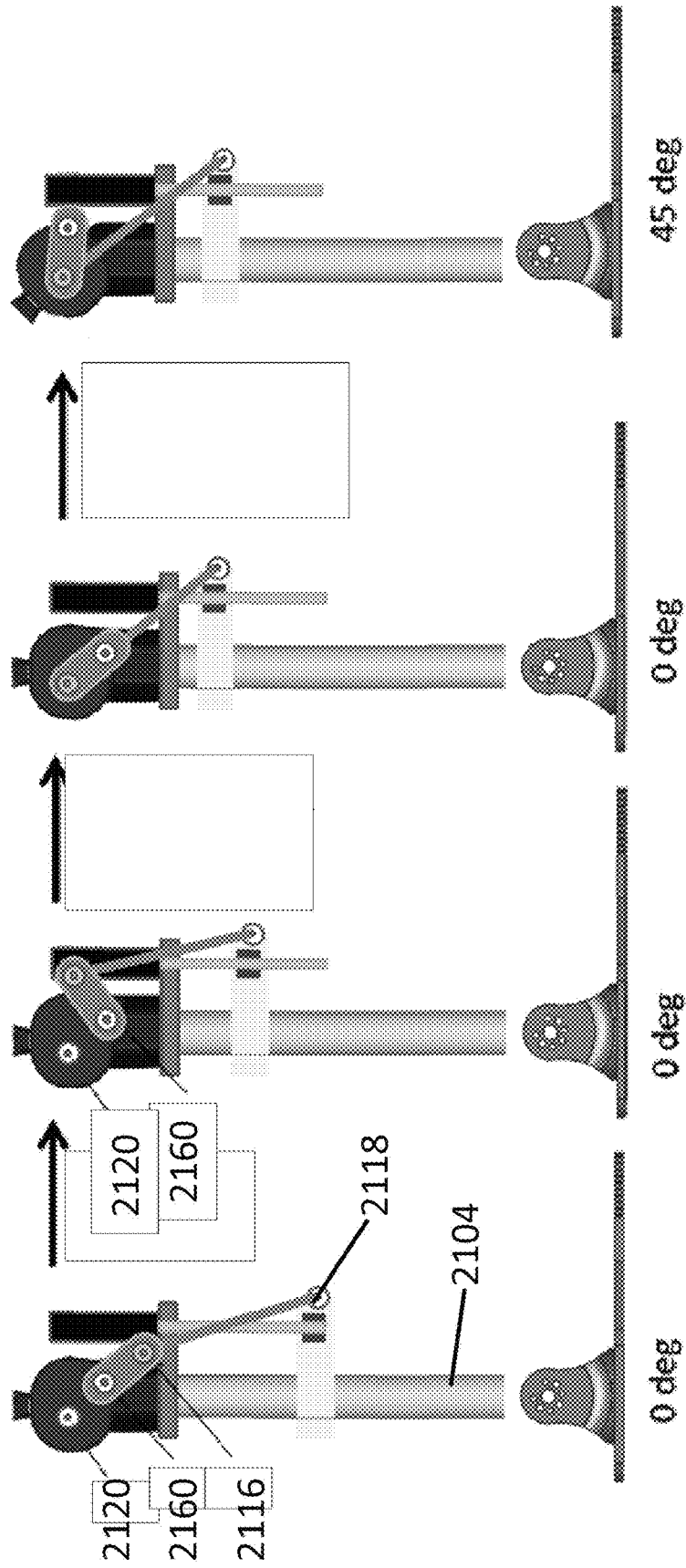

POWERED AND PASSIVE ASSISTIVE DEVICE AND RELATED METHODS

RELATED APPLICATIONS

This application claims benefit to U.S. Provisional Patent Application 62/088,849 filed on Dec. 8, 2014, which is incorporated by reference.

FEDERALLY SPONSORED RESEARCH OR DEVELOPMENT

The invention was made with government support under contract H133E130020 awarded by the National Institute on Disability and Rehabilitation Research of the U.S. Department of Education. The government has certain rights in the invention.

MICROFICHE/COPYRIGHT REFERENCE

[Not Applicable]

FIELD OF THE INVENTION

The application relates generally to the field of assistive devices, and particularly to assistive devices such as lower limb prostheses, orthoses, or exoskeletons.

BACKGROUND OF THE INVENTION

An above-knee amputation is a highly debilitating condition. Transfemoral amputees exert as much as twice the energy of their counterparts with fully intact lower limbs when walking on level ground. Tasks such as climbing stairs or standing up from a seated position are exceedingly more difficult for transfemoral amputees.

Passive prosthetic knees provide some support for walking. Some passive prosthetic knees incorporate microprocessor devices to intelligently control the compliance of the knee. A passive prosthetic knee does not provide additional power to the knee beyond the power provided by its user. A user of a passive prosthetic knee must compensate to adapt to the lost knee power during walking and while performing other tasks. For instance, a user of a passive prosthetic knee may lead with his or her sound limb when climbing curbs or stairs. As another example, users of passive prosthetic knees will "side step" up or down ramps. Some users of passive prosthetic knees do not have the strength to perform these tasks by compensating for the lack of power from the knee. In particular, elderly transfemoral amputees generally do not have the strength to use a passive prosthetic knee. As a result, many elderly transfemoral amputees, particularly those without family support, live in nursing homes rather than their own homes.

A powered prosthetic knee can provide a user with lost functionality by providing power similar to power provided by a biological knee. One commercially available powered prosthetic knee is the Power Knee by Össur (Reykjavik, Iceland), which uses a motor to provide the power. A powered prosthetic knee can give more functionality to its user. However, in the prior art, the added functionality comes at the cost of a prosthetic knee with greater weight. For example, the Power Knee weighs 3.19 kg (7.1 lbs), more than twice that of most passive prosthetic knees. The extra weight in a powered prosthetic knee is in the motor, transmission, and battery needed to provide sufficient power over a reasonable period of time. The user must carry this extra weight when walking, climbing stairs, or performing other tasks.

To date, powered prostheses have not improved the efficiency of gait. We believe this is due to the extra weight of powered prostheses in the prior art, including weight from the motor, transmission, and battery. Powered lower limb prostheses improve a user's ability to climb stairs, but most people do not climb stairs during much of the day. The ability to climb stairs and perform other tasks that require a powered prosthetic knee is important to accomplish many activities of daily living, but such tasks make up a relatively small portion of a user's daily mobility needs.

BRIEF SUMMARY OF THE INVENTION

In an embodiment, an assistive device is disclosed for replacing or augmenting the limb of an individual. The assistive device may comprise a joint and an actuator linkage. The actuator linkage may have a link portion that is movable to a first position coaxial to the joint or to a second position at a distance from the joint, and the actuator linkage may apply a torque to the joint when the link portion is positioned at the second position.

In one aspect, the actuator linkage applies the torque to the joint through the link portion.

In one aspect, the assistive device further comprises an adjustable linkage. The adjustable linkage may extend from the joint to a predetermined end position. The link portion may be movable along the adjustable linkage between the first position and the second position.

In one aspect, the actuator linkage may comprise a linear actuator. In one aspect, the joint may be flexible without actuation of the linear actuator when the link portion is in the first position. The joint may be extendable without actuation of the linear actuator when the link portion is in the first position. The joint may be flexible and extendable without actuation of the linear actuator when the link portion is in the first position.

In one aspect, the second position of the link position is a predetermined position.

In one aspect, the link portion is movable to a plurality of positions between the first position and the second position.

In one aspect, the assistive device may comprise a motor for actuating the linear actuator, the linear actuator being positioned so that the actuating axis of the linear actuator is parallel to the axis of the motor.

In one aspect, the actuator linkage may further comprise a crank member having a first end attached to the linear actuator and a second end being the link portion.

In one aspect, an outer face of the motor is in contact with a portion of the assistive device to dissipate heat generated by the motor.

In another embodiment, an assistive device for replacing or augmenting the limb of an individual may comprise a joint and a powered system. The powered system may have a first configuration in which the powered system rotates the joint by applying power to the joint, and a second configuration that allows for rotation of the joint without actuation of the powered system. The powered system may comprise a motor. The powered system may further comprise a linear actuator. An outer face of the motor may be in contact with a portion of the assistive device to dissipate heat generated by the motor.

The assistive device may be a prosthesis, such as an upper-limb prosthesis, a lower-limb prosthesis, or an ankle prosthesis. The assistive device may be an orthosis, such as an upper-limb orthosis or a lower limb orthosis, such as a knee orthosis.

In an embodiment, a method for operating an assistive device for replacing or augmenting the limb of an individual comprises receiving a first set of information indicating that the assistive device will operate in a powered task in a first gait cycle; engaging a powered system to provide power to a joint of the assistive device; providing power to the joint when the assistive device is operating in the powered task; receiving a second set of information indicating that the assistive device will operate in a passive task in a second gait cycle; and disengaging the powered system in response to the second set of information.

In an aspect, the step of engaging a powered system to provide power to a joint of the assistive device comprises moving a link portion of an actuator linkage from a first position coaxial to the joint to a second position at a distance from the joint.

In an aspect, the step of providing power to the joint when the assistive device is operating in the powered task comprises actuating a linear actuator.

In an aspect, the step of disengaging the powered system in response to the second set of information comprises moving a link portion of an actuator linkage from a second position at a distance from the joint to a first position coaxial to the joint.

In an embodiment, an assistive device is disclosed for replacing or augmenting the limb of an individual. The assistive device may comprise a joint and a powered system; the powered system having a first configuration in which the powered system rotates the joint by applying power to the joint; and a second configuration that allows for rotation of the joint without actuation of the powered system.

In an aspect, the powered system is in the first configuration when the assistive device is performing a powered task and the powered system is in the second configuration when the assistive device is performing a passive task.

In an aspect, the assistive device comprises a damper for the joint.

In an aspect, the actuator linkage has a link portion that is movable to a first position coaxial to the joint or to a second position at a distance from the joint. The actuator linkage may apply power to the joint when the link portion is positioned at the second position.

In an aspect, the assistive device may further comprise an adjustable linkage extending from the joint to a predetermined end position; the link portion being movable along the adjustable linkage between the first position and the second position.

In an aspect, the actuator linkage of the assistive device may comprise a linear actuator and a motor. The linear actuator may be positioned so that the actuating axis of the linear actuator is parallel to the actuating axis of the motor.

The actuator linkage may further comprise a connecting rod with a first end connected to the linear actuator and a second end being the link portion.

In an aspect, a motor of the assistive device may have an outer face that is in contact with a portion of the assistive device to dissipate heat generated by the motor.

In an aspect, the link portion of the actuator linkage is further movable to one of a plurality of positions between the first position and the second position.

Other aspects of embodiments of the invention are disclosed in the following specification, including the claims and figures.

BRIEF DESCRIPTION OF SEVERAL VIEWS OF THE DRAWINGS

FIGS. 11A, 11B, and 11C each displays a side view of a schematic representation of embodiments of an assistive device with respect to certain motor and linkage configurations.

FIGS. 12A, 12B, and 12C each displays a side view of a schematic representation of embodiments of an assistive device in different positions of flexion.

FIG. 19A displays a side view of an embodiment of an assistive device employing an offset slider crank configuration. FIG. 19B displays a frontal view of an embodiment of an assistive device employing an offset slider crank configuration. FIG. 19C displays a kinematic representation of an embodiment of an assistive device employing an offset slider crank configuration.

FIG. 20A displays a side view of an embodiment of an assistive device employing an offset slider crank configuration at zero degrees. FIG. 20B displays a side view of an embodiment of an assistive device employing an offset slider crank configuration at 45 degrees. FIG. 20C displays a side view of an embodiment of an assistive device employing an offset slider crank configuration at ninety degrees.

FIGS. 21A, 21B, 21C, and 21D each display a side view of an embodiment of an assistive device with varying positions of a motor and liner actuator.

FIG. 22A displays a side view of an embodiment of an assistive device employing a prismatic joint configuration at zero degrees. FIG. 22B displays a side view of an embodiment of an assistive device employing a prismatic joint configuration at 45 degrees. FIG. 22C displays a side view of an embodiment of an assistive device employing a prismatic joint configuration at 90 degrees.

FIGS. 23A and 23B each display a side view of an embodiment of a switching mechanism. FIGS. 23C and 24D each display a top view of an embodiment of a switching mechanism.

FIGS. 25A and 25B each displays a side view of an embodiment of a movable pin joint for an assistive device.

FIGS. 26A and 26B each displays a side view of an embodiment of a pawl ratchet switching mechanism for an assistive device.

FIGS. 27A-D each display a side view of an embodiment of an assistive device employing a singularity configuration.

DETAILED DESCRIPTION OF THE INVENTION

Figure 1:
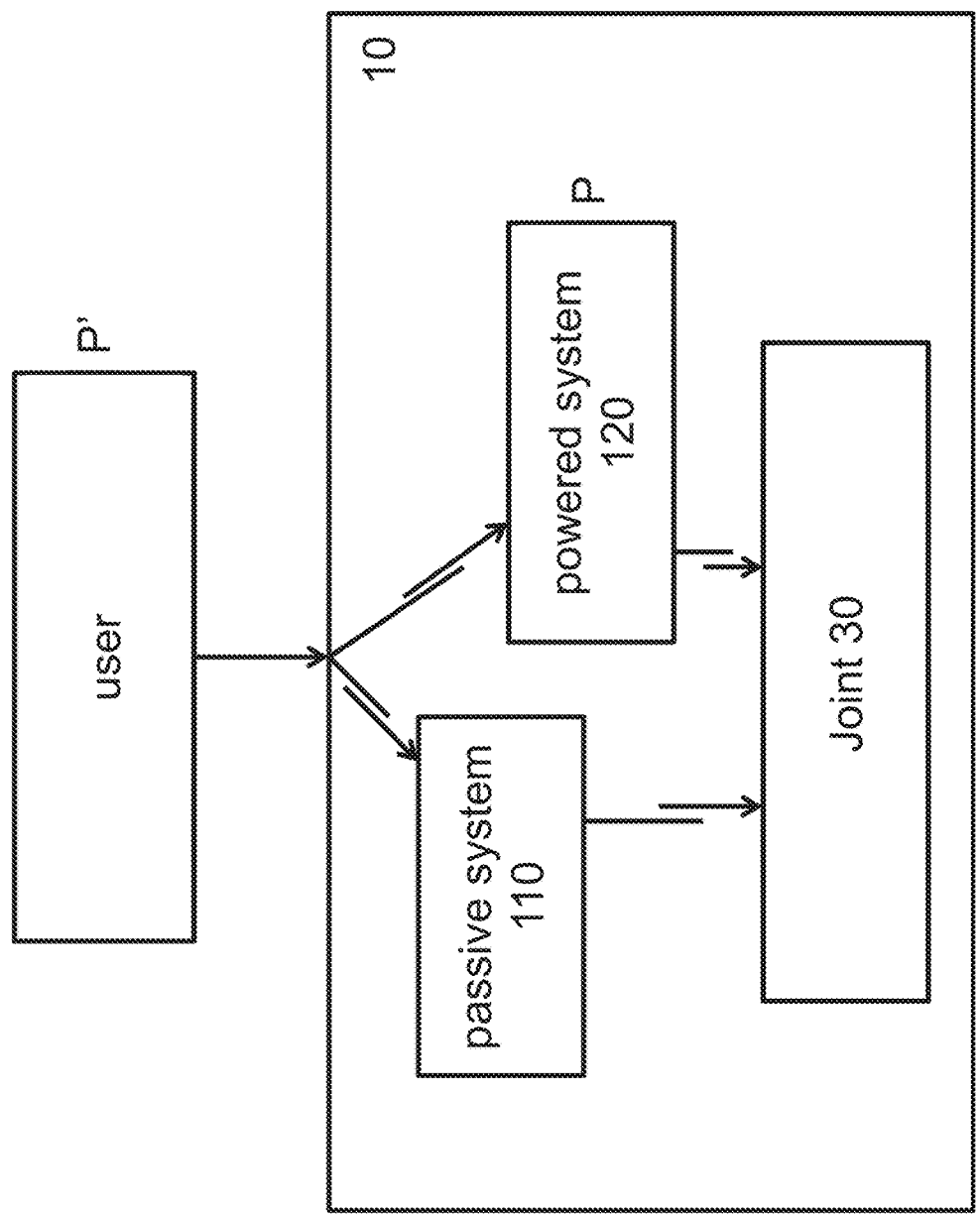
FIG. 1 displays a diagram of one embodiment of the assistive device.

In one embodiment, the assistive device comprises a lightweight, lower-limb prosthesis.

In one embodiment, the assistive device operates in a first configuration, known as a powered mode, and in a second configuration, known as a passive mode. The assistive device operates in a powered mode when it operates a powered task and in a passive mode when it operates a passive task. In the powered mode, the assistive device provides additional power to one or more of its joints. In the passive mode, the assistive device does not provide additional power to one or more of its joints. The transition between powered mode and passive mode is used herein to refer to a change in the configuration of the assistive device in order to transition between operating a powered task and a passive task. A mode may have mechanical aspects, so that the mechanical configuration of the assistive device differs between the powered mode and the passive mode.

A powered task is a task that requires additional power to a joint of the assistive device beyond the power a user provides. Examples of powered tasks may include sit-to-stand transfers, stair climbing, ramp ascent or descent, hill ascent or descent, curb ascent or descent, running, repositioning, and kneel-to-stand transfers. Tasks in which the assistive device operates to react to unexpected events that could be dangerous for the user, such as tripping, scuffing, or collapsing during walking or static support of the user's body weight, are also considered powered tasks.

A passive task is a task that does not require additional power to a joint of the assistive device beyond the power a user provides. One example of a passive task is level ground walking, except where a user wishes to walk more quickly than he or she can using body power alone, in which case walking becomes an active task.

The assistive device may switch between a powered task and a passive task, for instance, in response to information collected using sensors coupled to the assistive device. One method of switching between a powered task and a passive task in response to information collected from such sensors is disclosed in pending U.S. patent application Ser. No. 13/925,668 to A. Young and L. Hargrove, Ambulation Controller for Assistive Device, filed Jun. 24, 2013 (herein known as "the Young/Hargrove application"), which is incorporated by reference. Another method of switching between a powered task and a passive task is to have the user switch by pressing a button on a remote that is in operative communication with the assistive device. Other methods that may be used to control the assistive devices described herein are described in pending U.S. patent application Ser. No. 14/853,577 to T. Lenzi et al., Stance Controller and Related Methods, filed Sep. 14, 2015, which is incorporated by reference, and pending U.S. patent application Ser. No. 14/839,309 to T. Lenzi et al., Minimum Jerk Swing Control Assistive Device, filed Aug. 28, 2015, which is incorporated by reference.

One embodiment of the assistive device is shown in FIG. 1. The assistive device 10 may comprise a passive system 110 and a powered system 120, as shown in FIG. 1. The passive system 110 and the powered system 120 may operate in parallel. In one embodiment, the passive system 110 may be employed for passive tasks and the powered system 120 may be employed for powered tasks. A portion of the passive system 110 may be employed for powered tasks and a portion of the powered system 120 may be employed for passive tasks. Certain elements of the assistive device 10 may be common to both the passive system 110 and the powered system 120. Path flows of power from the user, through assistive device 10, to a joint, such as joint 30, may be engaged or disengaged, for instance by a clutch, as indicated by the broken arrows in FIG. 1.

As shown in the embodiment of FIG. 1, the user of the assistive device may provide power P' to joint 30 and the powered system 120 may provide power P to joint 30. Power P may be, for example, a torque applied to joint 30. The power P may complement the power P'.

Figure 2:
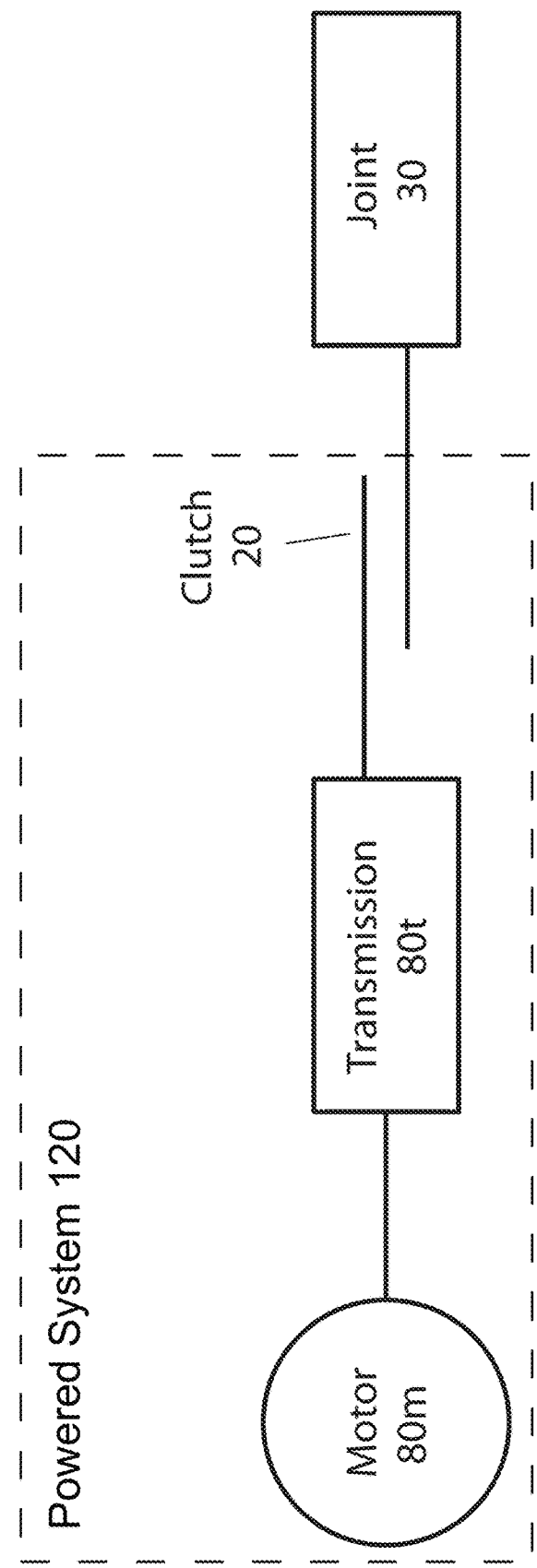
FIG. 2 displays a diagram of one embodiment of a motor train for use in the assistive device.

FIG. 2 displays one embodiment of a motor train for use in an assistive device. As illustrated in FIG. 2, the powered system 120 comprises a motor train to transmit power to joint 30. The powered system 120 may comprise a motor 80m and a transmission 80t. When the motor 80m actuates, the powered system 120 produces power P. When the transmission 80t actuates, the powered system 120 provides power P to joint 30. Transmission 80t may be engaged or disengaged by clutch 20 to joint 30. As shown in FIG. 2, clutch 20 is located between transmission 80t and joint 30. Alternately, clutch 20 could be located between motor 80m and transmission 80t, or at another suitable location. In one embodiment, the assistive device 10 is configured so that the transmission 80t actuates to provide power P to joint 30 only when the assistive device 10 is operating in a powered task.

Figure 3:
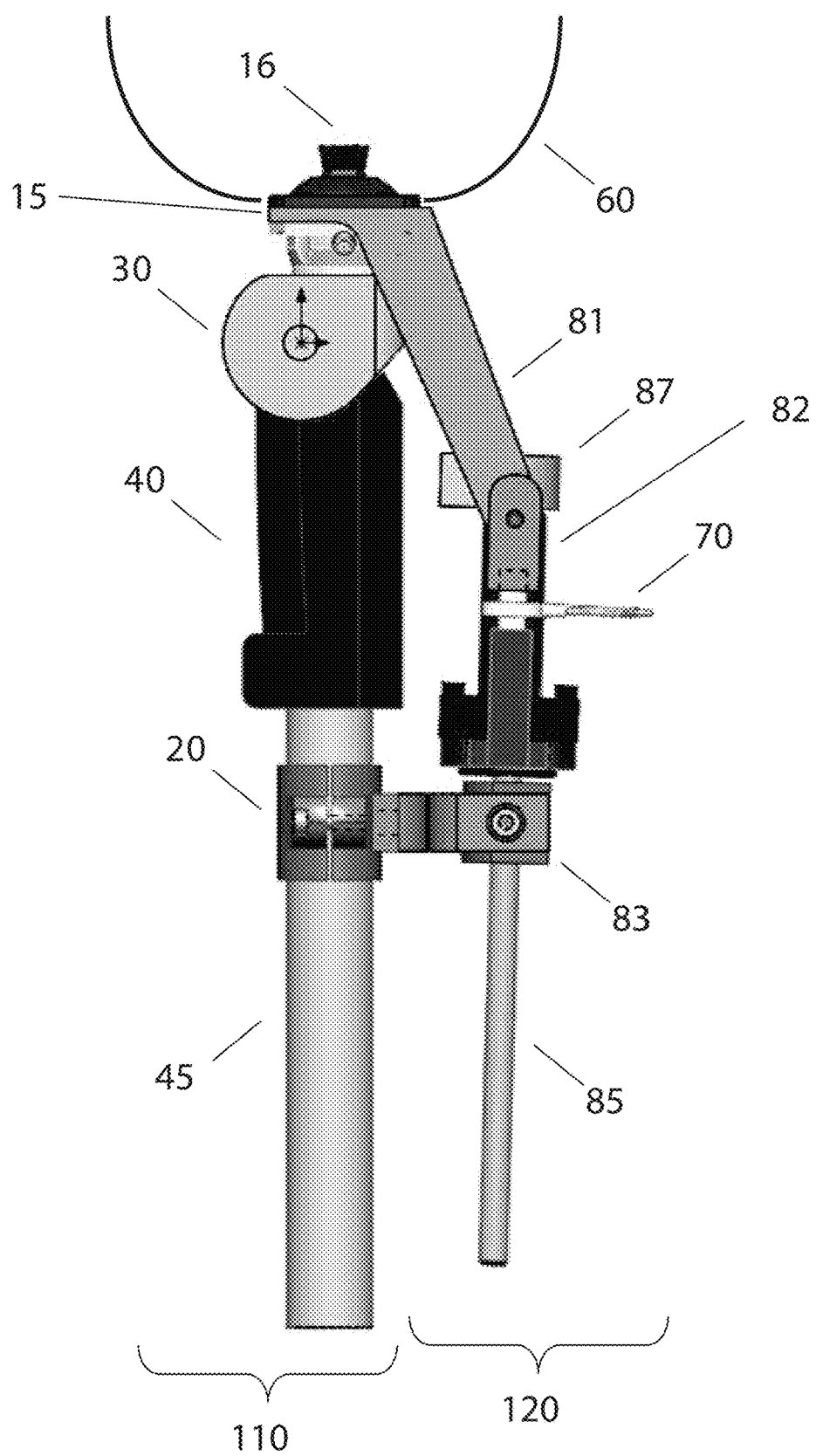
FIG. 3 displays a side view of one embodiment of the assistive device.

FIGS. 3-7 display one embodiment of assistive device 10, wherein assistive device 10 is a lower limb prosthesis. As illustrated in FIG. 3, assistive device 10 may comprise a knee joint 30. Knee joint 30 may further comprise damper 40. Assistive device 10 may also further comprise a passive system 110 having an upper leg portion 15 and a lower leg portion 45. Upper leg portion 15 may comprise a fastener 16 for attachment to socket 60. The user dons assistive device 10 by wearing socket 60 over her residual lower limb. Lower leg portion 45 may comprise a pylon. In one embodiment, knee joint 30 is provided by the Modular Knee Joint 3R95 from by Ottobock (Duderstadt, Germany). Damper 40 provides resistance during movement of assistive device 10. It should be understood that other damper embodiments are possible. For example, damper 40 may be hydraulic. In another embodiment, damper 40 may be mechanical, such as the damper provided in the Total Knee from Össur (Reykjavik, Iceland). In yet another embodiment, damper 40 may be pneumatic. Damper 40 may further comprise a spring that biases knee joint 30 to extension.

Figure 4:
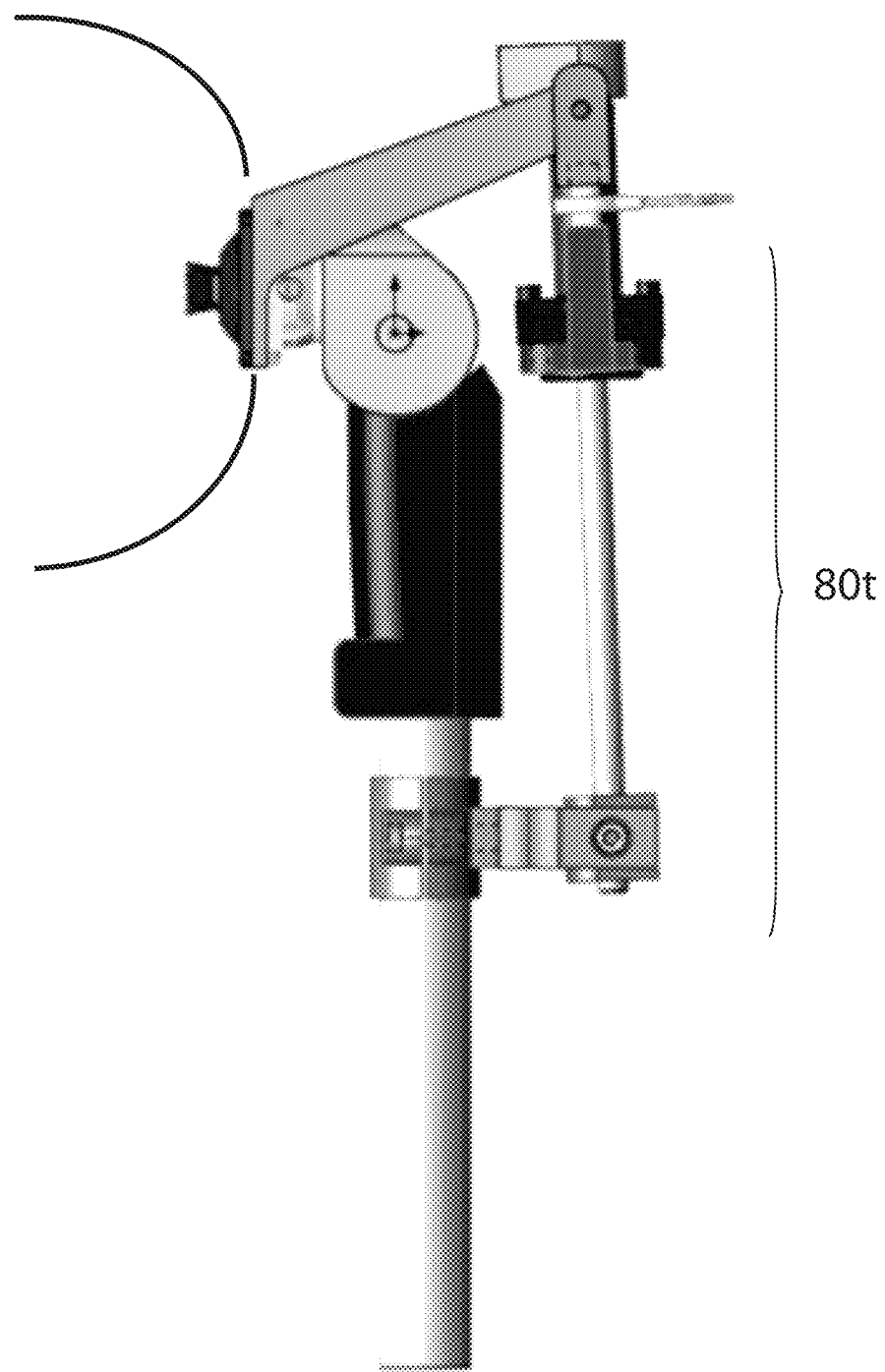
FIG. 4 displays another side view of one embodiment of the assistive device.
Figure 5:
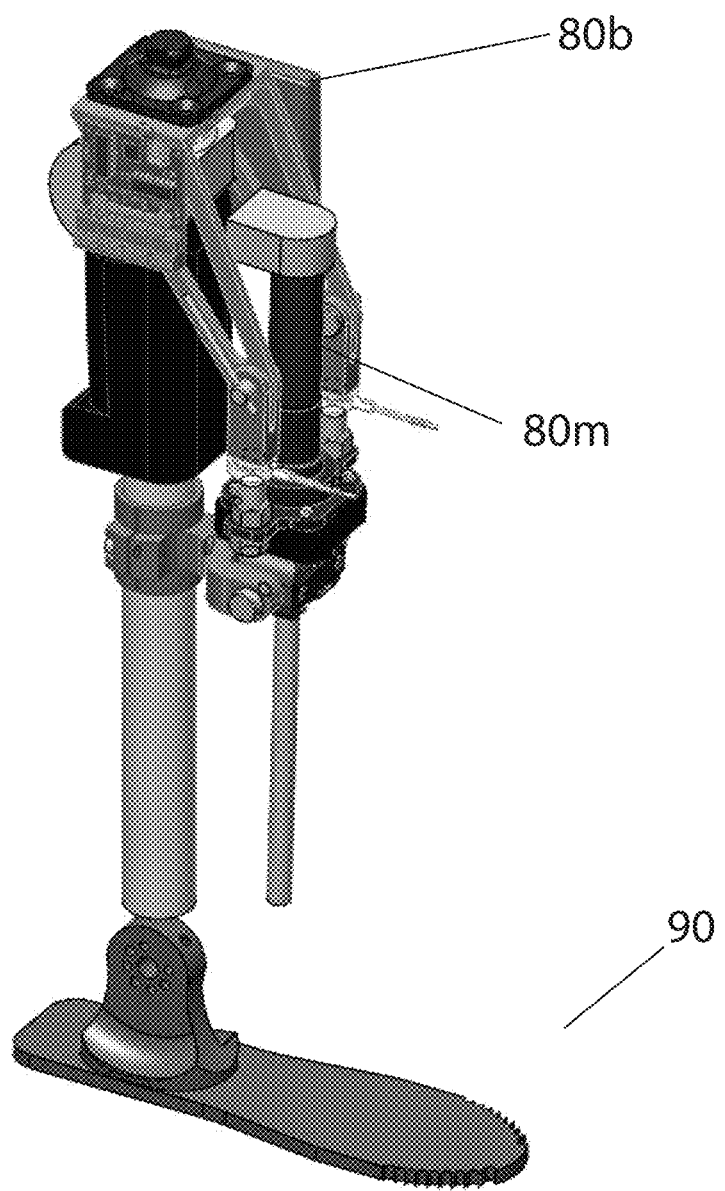
FIG. 5 displays a perspective view of one embodiment of the assistive device.
Figure 6:
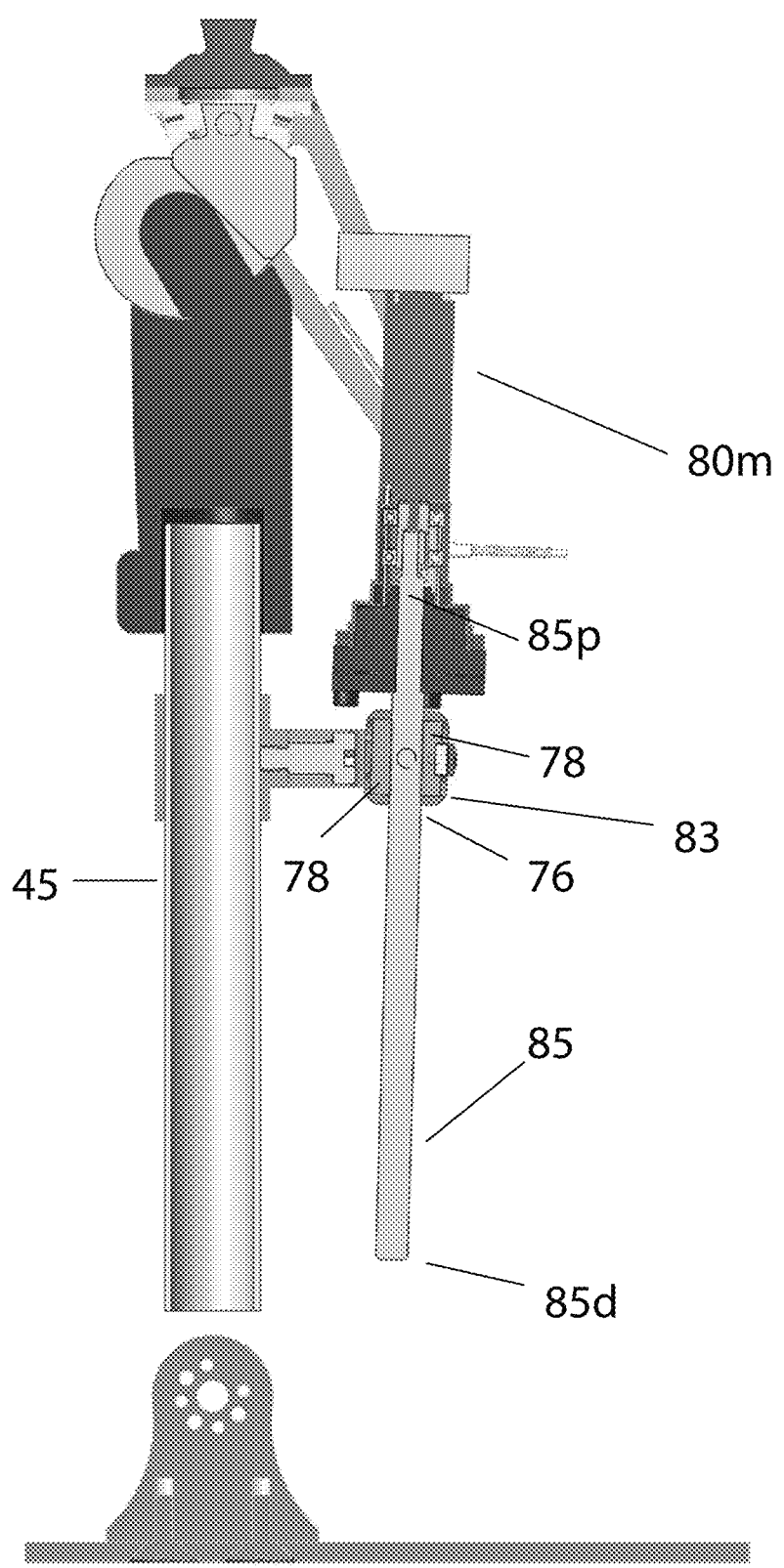
FIG. 6 displays a section view of one embodiment of the assistive device.

Assistive device 10 further comprises a powered system 120. In one embodiment, shown in FIGS. 3-7, the powered system 120 comprises a motor train and a linkage that may be used to provide power to the knee joint 30. As shown in FIGS. 4 and 5, the motor train may comprise a motor 80m, transmission 80t, and battery 80b. Battery 80b (further illustrated in FIG. 5) may provide power to motor 80m. Transmission 80t comprises linear actuator 85. As illustrated in FIG. 3, linear actuator 85 is positioned within a member 83. In one embodiment, illustrated in FIG. 6, member 83 comprises a housing having ball bearings 78 as well as shaft 76, which provides an opening through member 83. Linear actuator 85 is drivable through shaft 76, along ball bearings 78, and may be may be driven by motor 80m. As illustrated by FIG. 3, the linkage of powered system 120 comprises links 82 and 81, wherein link 82 is coupled to link 81 and link 81 is further coupled to upper portion 15 of passive system 110. Motor 80m may form part of link 82. The powered system 120 further comprises a clutch 20, which is coupled to member 83. Clutch 20 is engagable to lower leg portion 45. In one embodiment, clutch 20 comprises a clamp and linear actuator 85 comprises a ball screw.

Figure 10A:
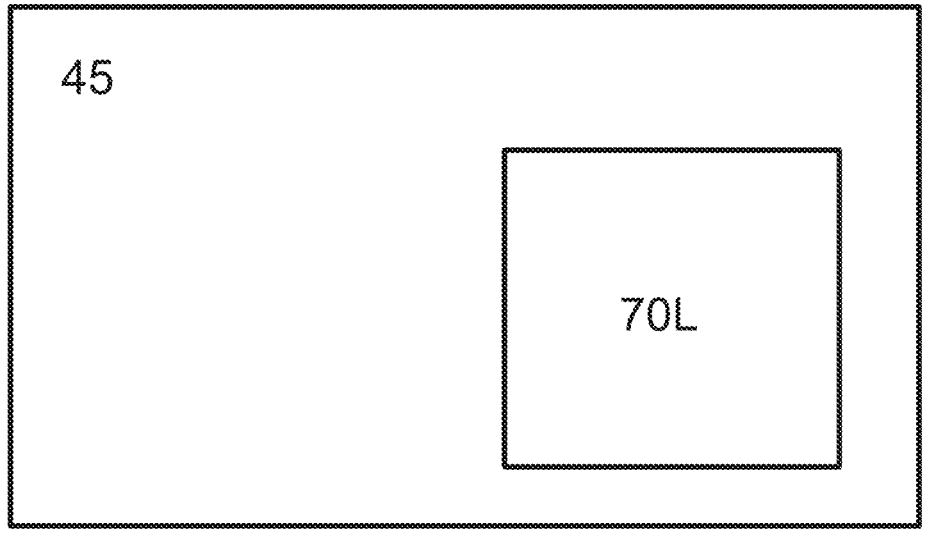
FIG. 10A displays a labeled representation of sensors on one embodiment of a lower leg portion.
Figure 10B:
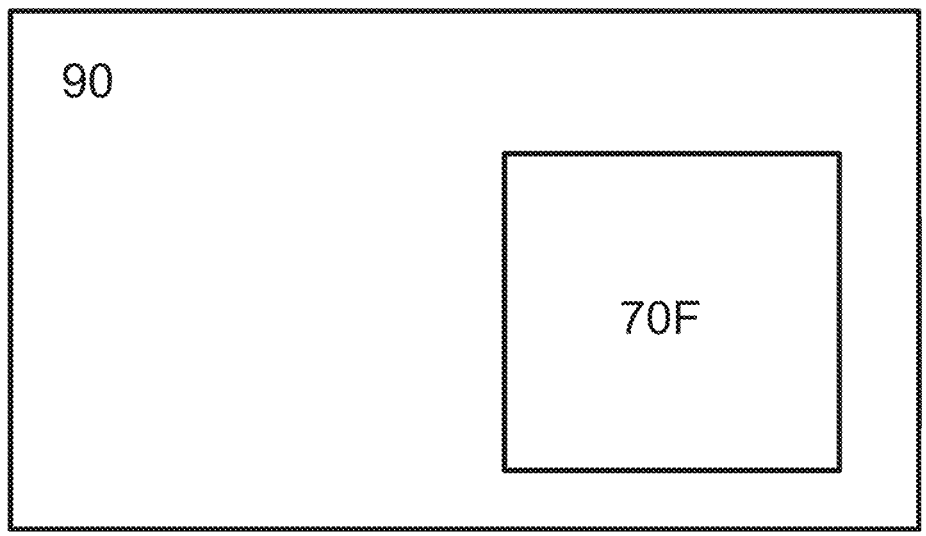
FIG. 10B displays a labeled representation of sensors on one embodiment of a foot.

The assistive device 10 is configured to actuate the powered system 120 when assistive device 10 operates in a powered task. In one embodiment, actuation of the powered system 120 comprises engagement of clutch 20 to lower leg portion 45. Clutch 20 may be configured to engage or disengage only when damper 40 bears the full load supported by assistive device 10. Sensors may allow assistive device 10 to measure the load supported by assistive device 10. In one embodiment, sensors may be positioned on the lower leg portion 45 and transmission 80t. In one embodiment, sensors 70L on lower leg portion 45 (illustrated at FIG. 10a) comprise strain gauges or Force Sensitive Resistor sensors, and sensors 70 on transmission 80t (illustrated in FIG. 3) comprise load cells. In another embodiment, sensors 70F may be placed under foot 90 (illustrated in FIGS. 5-6 and 10b). In one embodiment, sensors allow assistive device 10 to measure when the damper 40 is bearing the entire load supported by assistive device 10. In other embodiments, sensors allow assistive device 10 to measure when the damper 40 is bearing less than the full load supported by assistive device 10. In these embodiments, the clutch 20 may engage or disengage when damper 40 bears less than the full load supported by assistive device 10. Controller 150 (discussed below) uses information from sensors, for example sensors 70, to determine the appropriate time at which to engage or disengage clutch 20. In another embodiment, a determination of when to engage or disengage clutch 20 may be provided manually. For example, assistive device 10 may be in operative communication with a button which, when pressed by the user, causes the clutch 20 to engage or disengage.

When clutch 20 is disengaged from the lower leg portion 45, assistive device 10 relies on passive system 110. The power P' from the user's movement is transmitted through damper 40 so that the user may engage in level ground walking or another passive task.

When clutch 20 is engaged, the powered system 120 may provide additional power P to assist the user in performing a powered task. Linear actuator 85 is actuated by motor 80m, which in one embodiment is a direct current motor. Actuation of the linkage comprising link 81, link 82, member 83, linear actuator 85, and clutch 20 causes flexion and extension of knee joint 30. In one embodiment, linear actuator 85 may comprise a ball screw. In one embodiment, linear actuator 85 may have a proximal end 85p and a distal end 85d, illustrated in FIG. 6. As linear actuator 85 is actuated by motor 80m, linear actuator 85 translates through member 83, which drives links 82 and 81 to apply a force that causes flexion or extension of knee joint 30. In one embodiment, when the linear actuator 85 is actuated by motor 80m so as to flex knee joint 30 (illustrated in FIG. 4), the linear actuator is driven through shaft 76 along ball bearings 78 so that member 83 moves along linear actuator 85 towards linear actuator distal end 85d. When the ball screw of linear actuator 85 is actuated by motor 80m so as to drive the linkage to extend knee joint 30 (illustrated in FIGS. 3 and 6), the linear actuator 85 is driven through shaft 76 along ball bearings 78 so that member 83 moves along linear actuator 85 towards linear actuator proximal end 85p. In one embodiment, ball bearings 78 naturally hold linear actuator 85 in place, and prevent linear actuator 77 from sliding through shaft 76, when motor 80m is not activated.

The engagement/disengagement of clutch 20 has a low energy requirement because use of the powered system 120 is not needed during level ground walking. Because powered system 120 is relatively rarely employed by assistive device 10, the power required to employ powered system 120 each day is relatively low.

The transition between powered mode of assistive device 10 and passive mode of assistive device 10 is needed to switch between a passive task and an active task, for instance, in a transition between level-ground walking and stair ascent. Because the number of transitions needed to support a typical day of use is relatively low, clutch 20 undergoes limited engagement cycles and experiences low wear. As a result, the dimensions of the clutch 20 can be reduced. In one embodiment, clutch 20 is made of metal and weighs no more than 250 grams.

Figure 7:
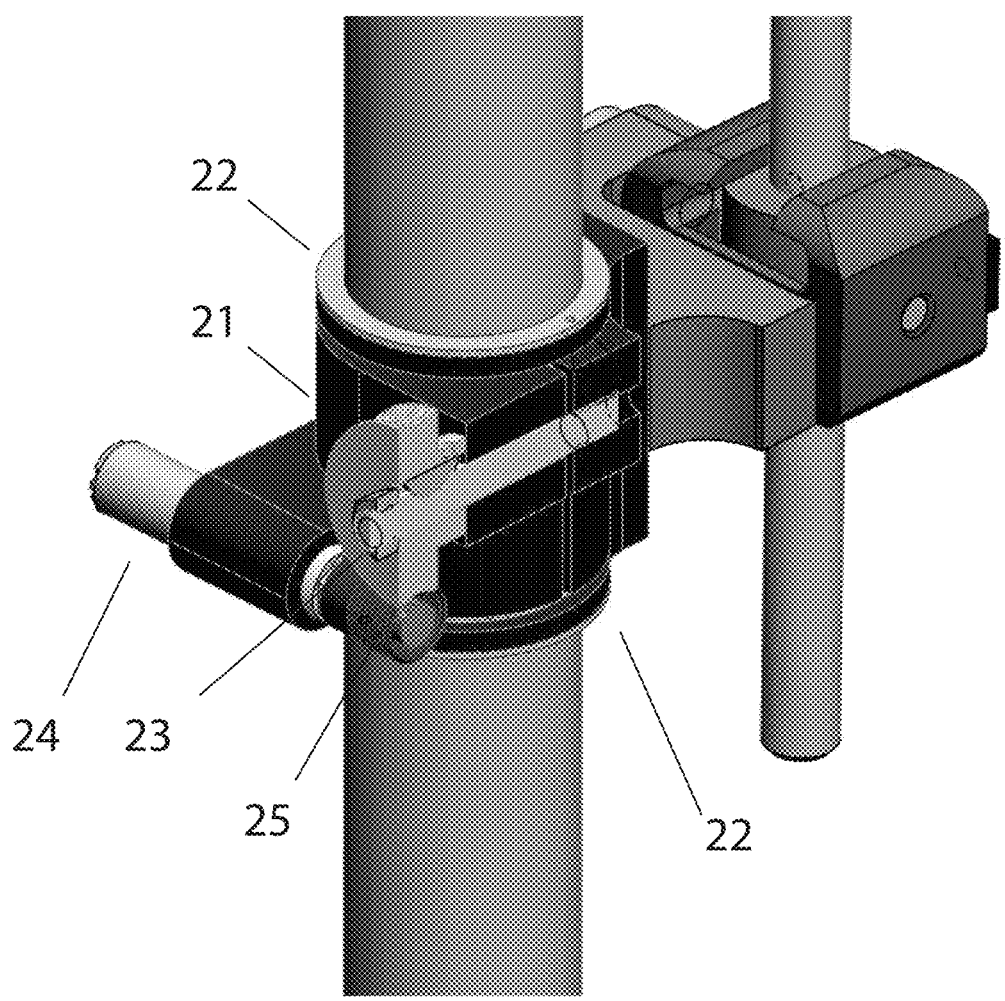
FIG. 7 displays a perspective view of one embodiment of a clutch for use in the assistive device.

FIG. 7 illustrates one embodiment of clutch 20. Clutch 20 is comprised of a collar 21, rings 22, screw 23, motor 24, and clutch transmission 25. In one embodiment, collar 21 is a high-friction clamping collar made of aluminum. In one embodiment, rings 22 are low-friction and made of plastic. In one embodiment, screw 23 is a set screw. In one embodiment, motor 24 is a DC motor. In one embodiment, clutch transmission 25 comprises a worm gear and a pinion gear. Motor 24 regulates the position of the screw 23 through clutch transmission 25. In turn, the position of screw 23 determines the effective diameter of collar 21. Adjustment of the angular position of motor 24, regulates the effective diameter of collar 21. When the diameter of collar 21 is greater than the diameter of lower leg portion 45, clutch 20 is disengaged from assistive device 10 and only rings 22 are in contact with the lower leg portion 45. Clutch 20, therefore, can slide up and down on lower leg portion 45. When the effective diameter of collar 21 is smaller than the nominal diameter of lower leg portion 45, such that collar 21 compresses lower leg portion 45, axial forces from friction between collar 21 and lower leg portion 45 hold clutch 20 in place, therefore engaging clutch 20. Clutch 20 may be connected to member 83 by a bolt arrangement or other appropriate connecting mechanisms.

The design specifications for battery 80b limit mobility of assistive device 10 to about 100 powered tasks, including sit-to-stand transfers, stair climbing, ramp ascent or descent, hill ascent or descent, curb ascent or descent, and kneel-tostand transfers. It should be understood that battery technology continues to improve, and future batteries may provide additional power without requiring additional weight. In one embodiment, the design specifications for battery 80*b* are such that the average user may climb up to 10 flights of stairs, or an equivalent combination of stairs, ramps and sit-to-stands (a sit-to-stand is comparable to taking one step on a flight of stairs). As the number of transitions needed to support a typical day of use is low, a small motor 80*m*, transmission 80*t*, and battery 80*b* may be used due to a small number of engagement cycles and low wear. For example, motor 80*m* may have a mass of 175 g, a peak torque of 1 Nm, a peak speed of 17000 rpm, a nominal voltage of 48V, and a nominal power of 120 W. Transmission 80*t*, for example, may weigh 400 g. Exemplary dimensions of ball screw 77 of transmission 80*t* are a 3 mm lead and a 10 mm diameter. Battery 80*b*, for example, may have a voltage of 48V and a weight of 100 g.

Controlling the Motor.

Figure 8:
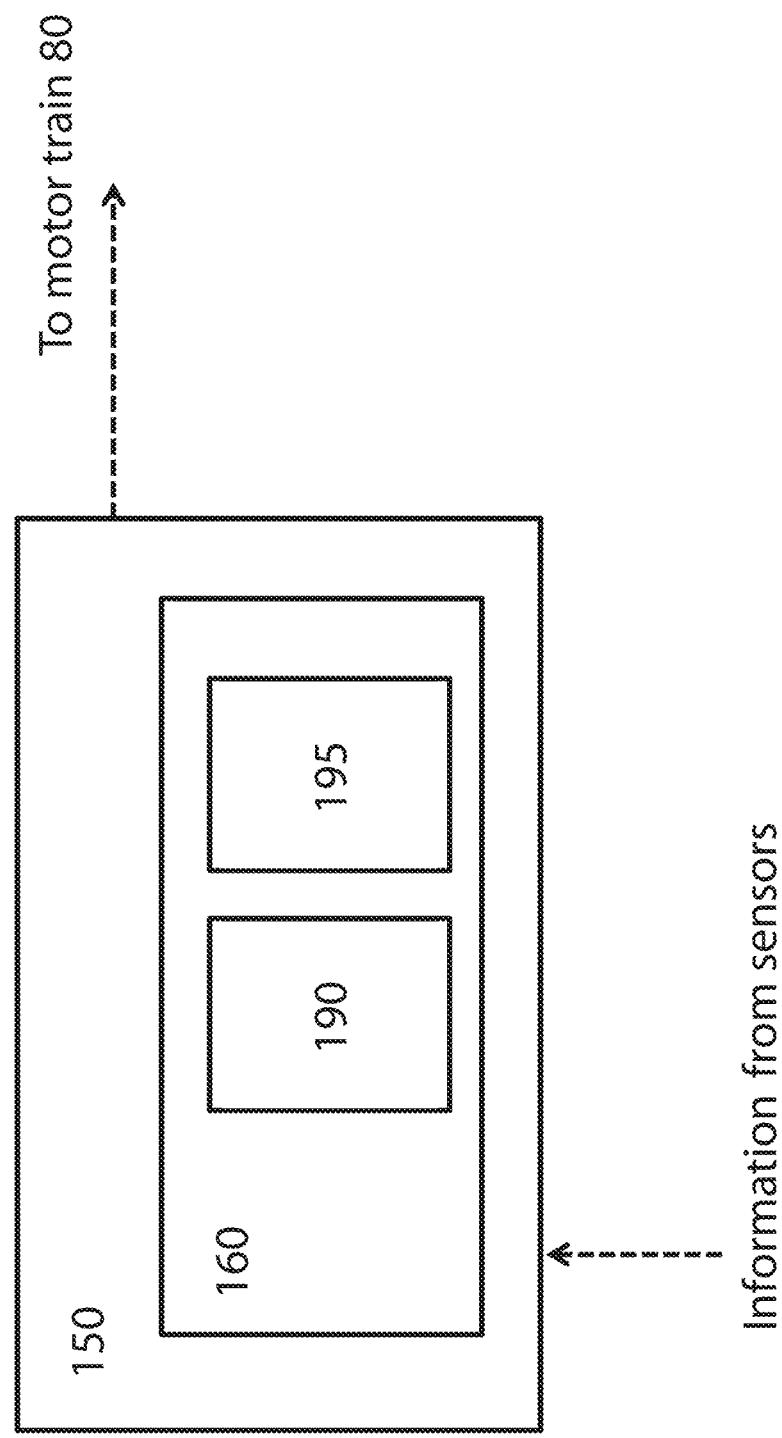
FIG. 8 displays a diagram of one embodiment of a controller for use in the assistive device.

Assistive device 10 may comprise controller 150. Controller 150 includes logic that drives motor train 80, which may include motor 80*m*, transmission 80*t*, and battery 80*b*. FIG. 8 displays a representation of controller 150. In one embodiment, controller 150 is connected to motor train 80. Controller 150 may comprise an off-the-shelf component, such as the Overo® Air Computer-On-Module (GUM3503A) offered by GumStix Inc. (Redwood City, Calif.) or a custom built component. Controller 150 comprises microprocessor 160, such as the Texas Instruments OMAP 3503 Applications Processor with processor speed of 600 MHz, or another appropriate microprocessor. Microprocessor 160 may comprise non-volatile memory 190 and RAM memory 195.

Controller 150 is programmed with logic to actuate motor train 80 when assistive device 10 is performing a powered task. In one embodiment, controller 150 may be a myoelectric controller that receives EMG information from the user that controller 150 uses to control assistive device 10. In another embodiment, controller 150 may use information from a set of sensors coupled to the assistive device 10, such as sensors 70 (illustrated in FIG. 3), in order to determine the appropriate task to perform.

In one embodiment clutch 20 could be manually actuated by the user, for example through a lever. In another embodiment, clutch 20 may be controlled by a computing device, such as a smart phone or a smart watch. In another embodiment, clutch 20 may be controlled by controller 150 in response to the detection of the user's intention to change ambulation mode (e.g., from walking to stair climbing), as shown for example in the Young/Hargrove application. Clutch 20 may be electrically connected to controller 150. Clutch 20 may have its own actuating mechanism, which may be a motor, solenoid, or other actuator. Communication between controller 150 and clutch 20 could be wired or wireless.

Clutch 20 may preferably be designed so that it is a low power device, thus saving additional weight to the overall assistive device 10. Trading weight for power may result in a clutch that engages and disengages more slowly (for instance, during a period of 200-300 ms) than a more powerful (and therefore heavier) clutch that would engage the lower leg portion 45 substantially more quickly. The engagement and disengagement of the clutch 20 may be performed at any point during the execution of a gait cycle in level-ground walking. This is possible because the passive system 110 of assistive device 10 allows completion of the gait cycle in level ground walking without requiring the motor 80*m* to be engaged and active. In other words, clutch 20 can be engaged and disengaged during the execution of the level-ground gait cycle without altering the movement of the knee joint 30. While the clutch 20 is engaging or disengaging, motor 80*m* may compensate for friction, viscosity, and inertia of transmission 80*t* so that the powered system 120 is providing a minimal amount of power, but still is not providing power to knee joint 30.

When transitioning from a powered task to a passive task (for example, from stair climbing to level-ground walking), the first gait cycle in level-ground walking can start with clutch 20 engaged but powered system 120 not providing power to knee joint 30. Clutch 20 may engage throughout the first step during the gait cycle. Motor 80*m* and transmission 80*t* are connected but are not providing power to knee joint 30. The passive system 110 is supporting the user's entire load and providing the required power for the user to walk. Because the engagement process is relatively slow, clutch 20 may rely on a smaller actuation system.

Figure 9:
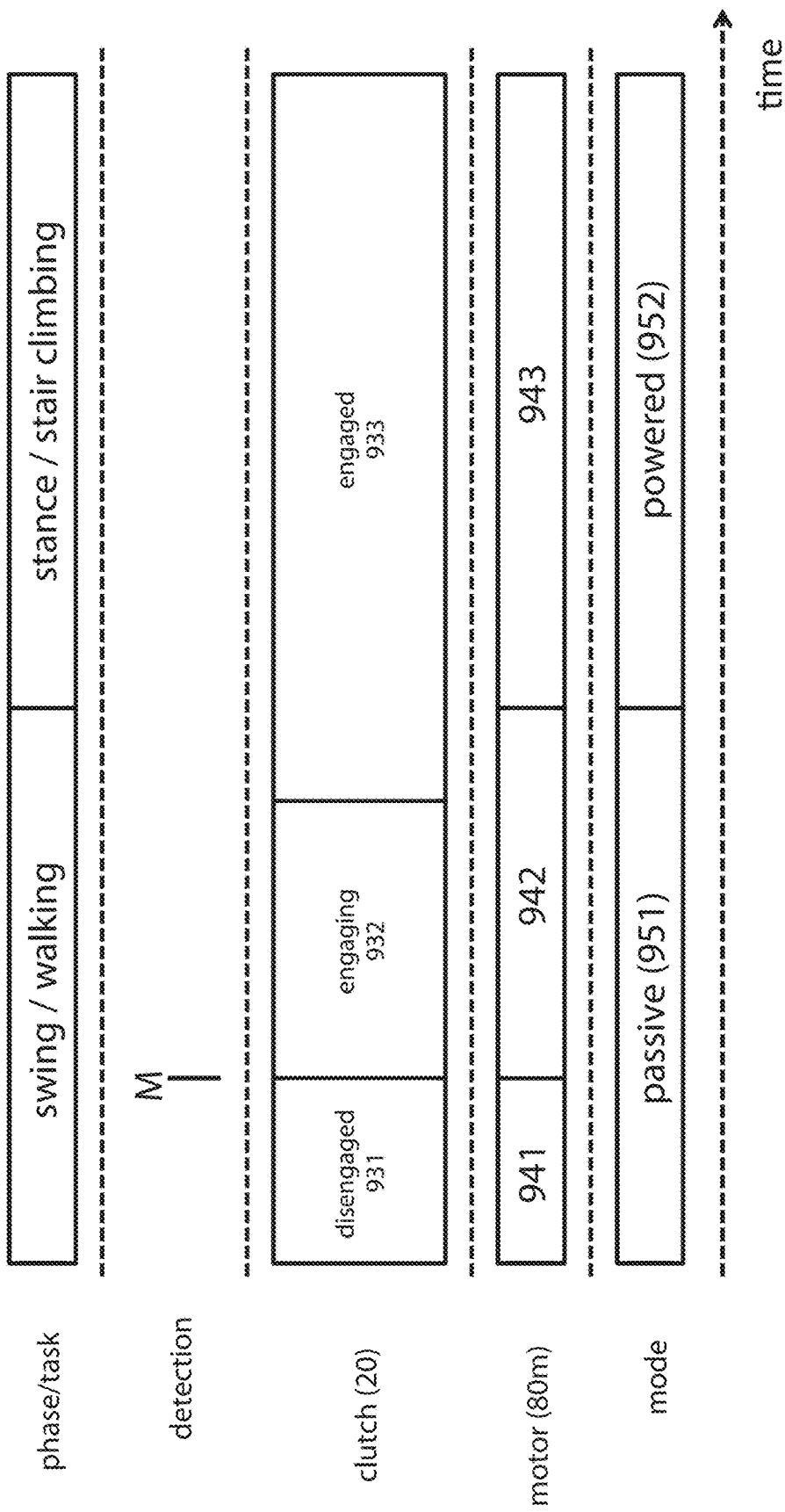
FIG. 9 displays a diagram of one possible transition from passive mode to powered mode of the assistive device.

Assistive device 10 may follow the control scheme illustrated in FIG. 9. When assistive device 10 is in powered mode, clutch 20 is engaged and motor 80*m* provides power to knee joint 30 as required by the specific task (e.g., stair climbing, sit-to-stand). When assistive device 10 is in passive mode, clutch 20 is disengaged and the motor is not providing power to knee joint 30. Additionally, assistive device 10 may have a transition mode, in which clutch 20 is engaging or disengaging but motor 80*m* is not providing power to knee joint 30. Assistive device 10 may be in transition mode at any point in the level-ground gait cycle.

Motor encoder 87 provides one or more feedback signals that track its position. Signals from motor encoder 87 are sent to controller 150, which uses the information in the signals to determine the position of knee joint 30. In one embodiment, the position of knee joint 30 is determined using kinematics of the linkage (for example, links 81 and 82) of the assistive device 10. For instance, knowing the position of motor encoder 87 and member 83 allows controller 150 to compute the position of knee joint 30. In other embodiments, sensors may be applied on knee joint 30 to determine its position, which may be an acceptable alternative even though additional sensors would increase the weight of assistive device 10.

One example of a transition from a passive mode to a powered mode, during a transition from walking to climbing stairs, is shown in FIG. 9. In this example, the user starts by walking on assistive device 10 and assistive device 10 is in walking mode (passive mode 951). Clutch 20 is disengaged (block 931) as the user is walking in this passive mode. While walking, the user nears a set of stairs. In the swing phase, prior to stepping on the first stair, a change in mode is detected. This detection is represented by M in FIG. 9. The change in mode may be detected as described in the Young/Hargrove application. Alternately, other means may be used to detect a change in the mode, such as receiving a signal from the push of a button coupled to assistive device 10 during a manual change in mode. Upon detection, clutch 20 begins to engage (block 932). Motor 80*m*, which was off during the earlier portion of the swing phase (block 941), begins to provide a small amount of power (block 942) to compensate for friction, viscosity, and inertia of transmission 80*t*. The net power provided by motor 80*m* in block 942 to the knee joint 30, however, is still about zero. Clutch 20 becomes fully engaged (block 933), which is represented in FIG. 9 as occurring before the end of swing phase but which may occur any time up to the start of stance phase of the stair climbing task (powered mode 952). On the start of the next gait cycle, assistive device 10 begins to operate in the stair climbing task (which, as shown in FIG. 9, begins with a stance phase). Motor 80*m* fully engages (block 943) and assistive device 10 transitions from passive mode (block 951) to powered mode (block 952). The additional power P provided by the powered system helps the user climb the stairs.

In another embodiment, the powered system 120 may be physically detachable and/or re-attachable from passive system 110 or otherwise from the assistive device. In such configuration, the powered system 120 could be configured to be used on passive assistive devices already available in the marketplace. Such a feature would allow a patient to select a passive assistive device of his or her preference from different commercial providers, and then attach it to a powered system 120 for improved performance over the passive assistive device alone.

Benefits.

Some benefits of the systems and methods described herein are apparent to one of ordinary skill in the art. A lightweight assistive device augments mobility but is not so heavy as to be a burden during operational use, such as walking or performing other tasks. The assistive device provides power for certain tasks that require power. In one embodiment, the assistive device does not provide power to the knee joint during level ground walking. In one embodiment, the assistive device provides power to the knee joint when performing a powered task such as sit-to-stand transfers, stair climbing, ramp ascent or descent, hill ascent or descent, curb ascent or descent, running, repositioning, and kneel-to-stand transfers. Because the assistive device provides power to the joint only during these or other similar powered tasks, the assistive device uses a lighter motor, battery, and/or transmission. The assistive device is therefore light enough to be tolerable for walking, while providing the functionality necessary to accomplish more demanding mobility needs.

The powered tasks are generally short in duration, compared to the thousands of level ground steps taken each day. Because of the short duration of powered tasks, and the option to limit the user to a reasonable maximum duration of powered tasks, assistive device 10 may include a much smaller motor because it is acceptable to overload motors for short periods of time. For instance, a user of the assistive device described herein may climb one to two consecutive flights of stairs at a time, and ten flights of stairs per day. Additionally, the infrequency of use of the motor will provide time for it to cool down between uses.

This system will also require much less onboard energy due to the relatively low number of powered tasks that people need to perform to navigate compared to the frequency of level ground walking over the course of a day. This means a smaller battery can be used to power the assistive device. A smaller battery coupled with a smaller motor allows for significant weight savings.

The motor and transmission are generally only used during the powered tasks, which are shorter in duration and limited in the number of iterations taken each day, compared to level ground steps and other passive tasks. Therefore, the motor and transmission will wear less than if they were used for level ground steps and other passive tasks. As a result, a smaller motor and transmission can be used, and significant weight savings can be realized. At the same time, the maintenance of the assistive device may be reduced, lowering the overall cost of the device.

Another embodiment of an assistive device is shown in FIG. 11. The assistive device 1000 comprises an upper part 1010 and a lower part 1020. The upper part 1010 and the lower part 1020 are connected through a knee joint 1030. In an embodiment, the knee joint 1030 may be a hinge joint. The lower part 1020 may be connected to a pylon 2000, such to extend the total length of the lower part 1020 in order to connect the knee joint 1030 to a foot component 3000. The motion of the knee joint 1030 around its axis may be achieved through a passive system 1100 and an active system 1200. The passive system 1100 and the active system 1200 may connect the lower part 1020 to the upper part 1010. In one embodiment, the passive system 1100 comprises a resistance element 1500. In various embodiments, the resistance element 1500 may be a friction element, a damper, a pneumatic device, or a hydraulic device. The resistance element 1500 applies resistance to slow the extension or flexion of the knee joint 1030. The resistance element 1500 may provide a constant resistance, a velocity dependent resistance, or another position dependent resistance. The resistance element 1500 may further comprise a biased spring in parallel to help the knee joint 1030 return to full extension after being flexed.

FIGS. 11A, 11B, and 11C each display a side view of a schematic representation of an embodiment of an assistive device. The figures display certain exemplary offset slider crank embodiments and possible arrangements of a motor for an assistive device. As shown in FIGS. 11A, 11B, and 11C, the motor 1310 may be placed in different locations in different embodiments of the assistive device. In one embodiment, as shown in FIG. 11B, the shaft of the motor 1310 can be directly attached to the screw 1320. In other embodiments, such as the embodiment shown in FIG. 11C, the shaft of the motor 1310 may drive the screw 1330 through a transmission 1340, which may be a synchronous transmission mechanism with mating rotating elements. As illustrated in the example of FIG. 11C, an actuating axis 1110 (e.g., an axis of the screw 1320) is parallel with a motor axis 1120. In one embodiment, the transmission 1340 may be a synchronous transmission mechanism, for instance one comprising a belt 1370, a pulley 1350, and a pulley 1360. The nut 1330 may be driven up and down along the screw 1320 by rotation of the motor 1310.

The slider 1220 may connect to the linear guidance 1260 through linear bearings, which in various embodiments may be recirculating ball bearings or plastic bushings, that allow the slider 1220 to slide freely up and down along the guidance 1260 (as shown in one embodiment in FIG. 13) without rotating with respect to said lower part 1020. Therefore, in one embodiment, the screw nut 1330 allows with its movement the motor 1310 to drive the slider 1220. Therefore, the linear actuator 1300 drives the active mechanism 1200. In various embodiments, the linear actuator may be pneumatic or hydraulic, although such systems (which may also require generators, compressors, and/or fluids) may add additional weight to the overall assistive device. In yet other embodiments, the linear actuator may be a piezo-electric actuator or a moving coil.

The assistive device 1000 may use sensors and a battery system similar to those already described for its control and operation. In one embodiment, the active system 1200 comprises a four-bar linkage in an offset inverted slider-crank configuration. A linear actuator 1300 is connected to the motor 1310, either directly as shown in FIG. 11B or by a transmission 1340 as shown in FIG. 11C. The linear actuator 1300 is coupled to a connecting rod 1210, which transmits the motion from the linear actuator 1300 to the crank 1230, which may be rigidly affixed to the upper part 1010. The connecting rod 1210 attaches to the crank 1230 with a rotational joint 1240. The screw 1320, the nut 1330, the connecting rod 1210, and a link portion (e.g., the rotational joint 1240) make up an actuator linkage 1380 that connects the transmission 1340 to the crank 1230. In an embodiment, the linear actuator comprises a screw 1320 and a nut 1330. The screw 1320 may be a ball screw, lead screw, roller screw, or other appropriate screw. A linear guidance 1260 and a slider 1220 may support the linear motion of the linear actuator 1300. The linear guidance 1260 may be rigidly attached to the lower part 1020, and the slider may be rigidly attached to the nut 1330, so that the linear guidance 1260 provides linear support to the nut 1330 as it travels along the length of the screw 1320. The connecting rod 1210 also may attach to a slider 1220 with a rotational joint 1250.

Figure 13:
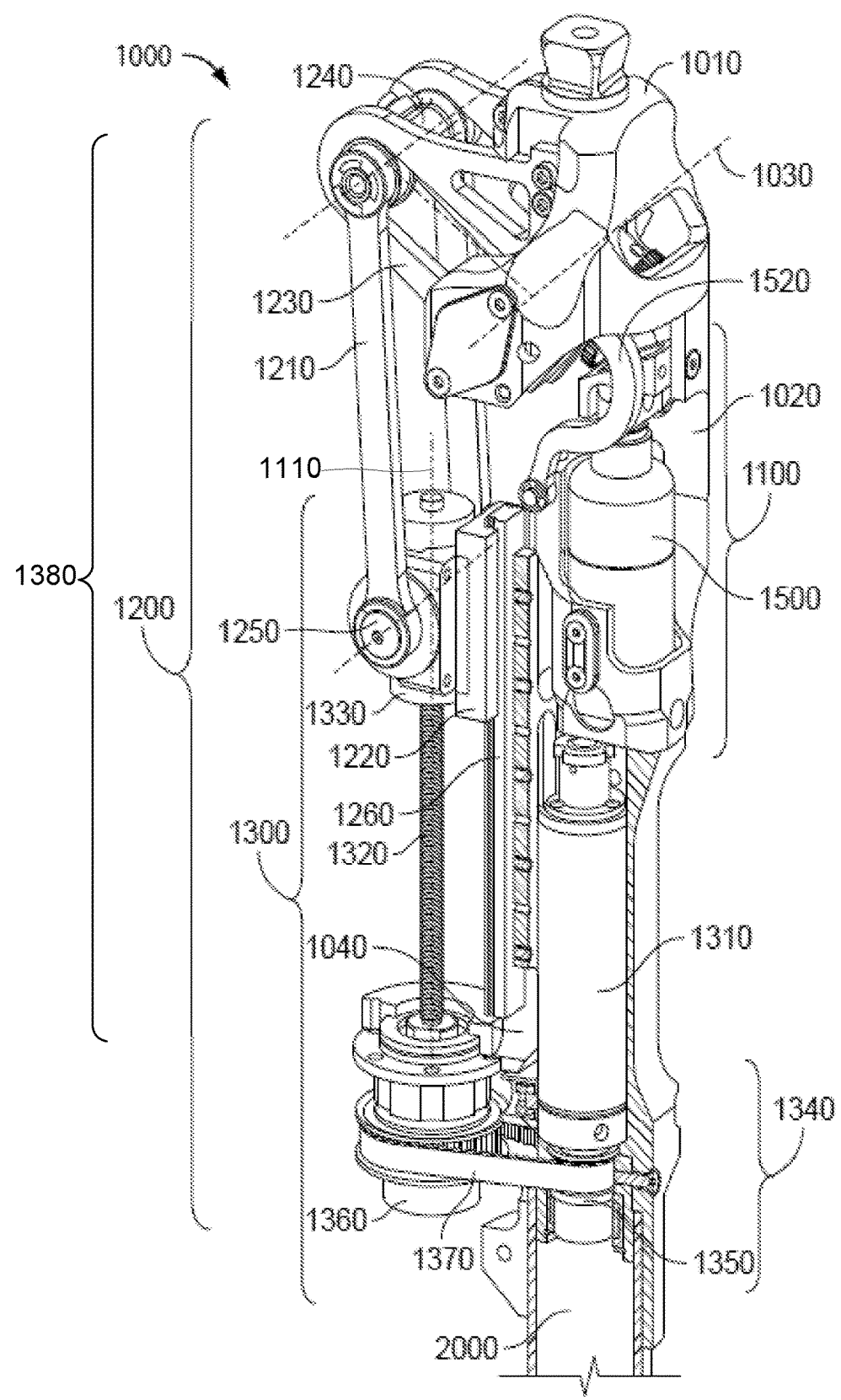
FIG. 13 displays a partial-sectioned view of an embodiment of an assistive device, displaying an internal motor arrangement and transmission.

FIG. 13 shows a partial sectioned view of an embodiment of the assistive device 1000. FIG. 13 shows the internal motor arrangement and the belt-tensioning mechanism of the transmission 1340. The linear actuator 1300 comprises a transmission 1340. In an embodiment, the transmission 1340 may be a synchronous transmission mechanism. For example, the transmission 1340 shown in FIG. 13 comprises two parallel-axes rotating elements synchronously mating, such that the motor 1310 and the screw 1320 have parallel axes. The transmission 1340 shown in FIG. 13 comprises a pulley 1350, a pulley 1360, and a belt 1370. The pulley 1350 is coaxial to the motor 1310 and the pulley 1360 is coaxial to the screw 1320. In an embodiment, the motor 1310 is located within the lower part 1020, for instance within the frame of the lower part 1020. In order to best dissipate heat from the motor 1310 into the frame of the lower part 1020, the frame of the lower part 1020 may be dimensioned so that the inside face of the frame of the lower part 1020 touches or is in contact with (such as in planar contact with) an outer face of the motor 1310. As the motor 1310 operates, the heat creates is dissipated through the surface of the lower part 1020.

The motor 1310 may be substantially aligned with the direction of the pylon 2000. Locating the motor 1310 in this way can minimize the weight asymmetry of the assistive device 1000 with respect to the sagittal plane and to the knee-foot direction. Other advantages include protecting the motor 1310 from external agents, dampening of the noise from the fast-spinning stages of the linear actuator 1300, and realization of a compact and rugged arrangement of the components, particularly keeping the motor 1310 and the screw 1320 parallel and within the same longitudinal encumbrance (shown, for instance, in FIG. 14). Batteries for the motor 1310 may be variously positioned. For instance, the batteries may be positioned in pairs, around the active component 1200, or in other appropriate positions.

The assistive device 1000 may further include a mounting frame 1040 which connects the linear guidance 1260 to the lower part 1020. The frame 1040 may be mounted at different distances away from the lower part 1020 and may be mounted, for instance, using setscrews and/or slotted holes and bolts, as shown in FIG. 15. Changing the set distance of the linear guidance 1260 from the lower part 1020 changes the inter-axes distance between the pulley 1350 and the pulley 1360, and provides an initial tension into the belt 1370.

FIGS. 12A, 12B, and 12C each displays a side view of a schematic representation of embodiments of an assistive device at 0, 45, and 90 degrees of flexion when the assistive device is in a powered mode. The knee angle is defined by the crank angle plus an angular offset depending upon the particular realization of the upper part 1010. The assistive device 1000 may be designed so that when the knee angle is at about 107 degrees, the nut 1330 is in a singularity with respect to the connecting rod 1210, to assist in the transition from sit to stand. Having the nut 1330 in singularity with the connecting rod 1210 provides a little play for the nut to move along the rod 1210 without requiring actuation by the motor 1310. Regardless of the particular configuration, the transformation between the angle of rotation of the motor 1310 and the angle of the crank 1230 depends upon the transmission of the linear actuator 1300, the offset e of the mechanism, the length a of the crank 1230 and the length b of the rod 1210. These values can be set by design to optimize the range of motion and torque/speed capability of the mechanism, for specific device applications. The particular inclination of the axis of the linear guidance 1260 with respect to the direction of the pylon 2000 does not affect the overall transmission of the active system 1200, and thus can be freely adjusted in order to meet other design criteria (such as shape size and arrangement of the components, structural requirements, aesthetical requirements, and other appropriate design criteria). In particular, in various embodiments, the linear actuator 1300 can be located in different positions. For example, the linear actuator 1300 can be located outside and in front of the lower part 1020, outside and behind the lower part 1020, or inside the lower part 1020, such as inside the pylon 2000.

The total transmission ratio (TR) is the product of two components: the TR of the linear actuator itself (how many millimeters of nut displacement correspond to 1 degree of motor rotation) and the TR of the kinematic chain (geometry- and position-dependent). The first one, itself, is given by the product of the TR of the pulley stage (revolution of driven pulley for 1 revolution of driving pulley) and the screw TR (millimeters of the lead). Table 1 below summarizes total transmission ratio (crank rotations/motor rotations), with the screw and the pulley for the design, and some variations over the geometry. These affect the shape of the TR-angle curve, which is shown in FIG. 18A, while a pulley TR of 42/18 and a screw TR of 2 mm/360 degrees only act as a uniform multiplication factor.

TABLE A

| Knee angle | Total TR | Plot numbering (FIG. 18A) | Offset of the mechanism e | Length of the crank a | Length of the rod b |
|---|---|---|---|---|---|
| 0 deg | 275 | 1810 | 32.5 mm | 45 mm | 100 mm |
| 30 deg | 330 | | | | |
| 60 deg | 296 | | | | |
| 90 deg | 137 | | | | |
| 108 deg | 0 | | | | |
| 0 deg | 245 | 1820 | 15 mm | 45 mm | 100 mm |
| 30 deg | 330 | | | | |
| 60 deg | 326 | | | | |
| 90 deg | 186 | | | | |
| 108 deg | 50 | | | | |
| 0 deg | 169 | 1830 | 32.5 mm | 25 mm | 100 mm |
| 30 deg | 183 | | | | |
| 60 deg | 149 | | | | |
| 90 deg | 59 | | | | |
| 108 deg | −13 | | | | |
| 0 deg | 264 | 1840 | 32.5 mm | 45 mm | 50 mm |
| 30 deg | 330 | | | | |
| 60 deg | 307 | | | | |
| 90 deg | 107 | | | | |
| 108 deg | −100 | | | | |
| (any) | 0 | (null) | 32.5 mm | 0 mm | 100 mm |

Figure 18A:
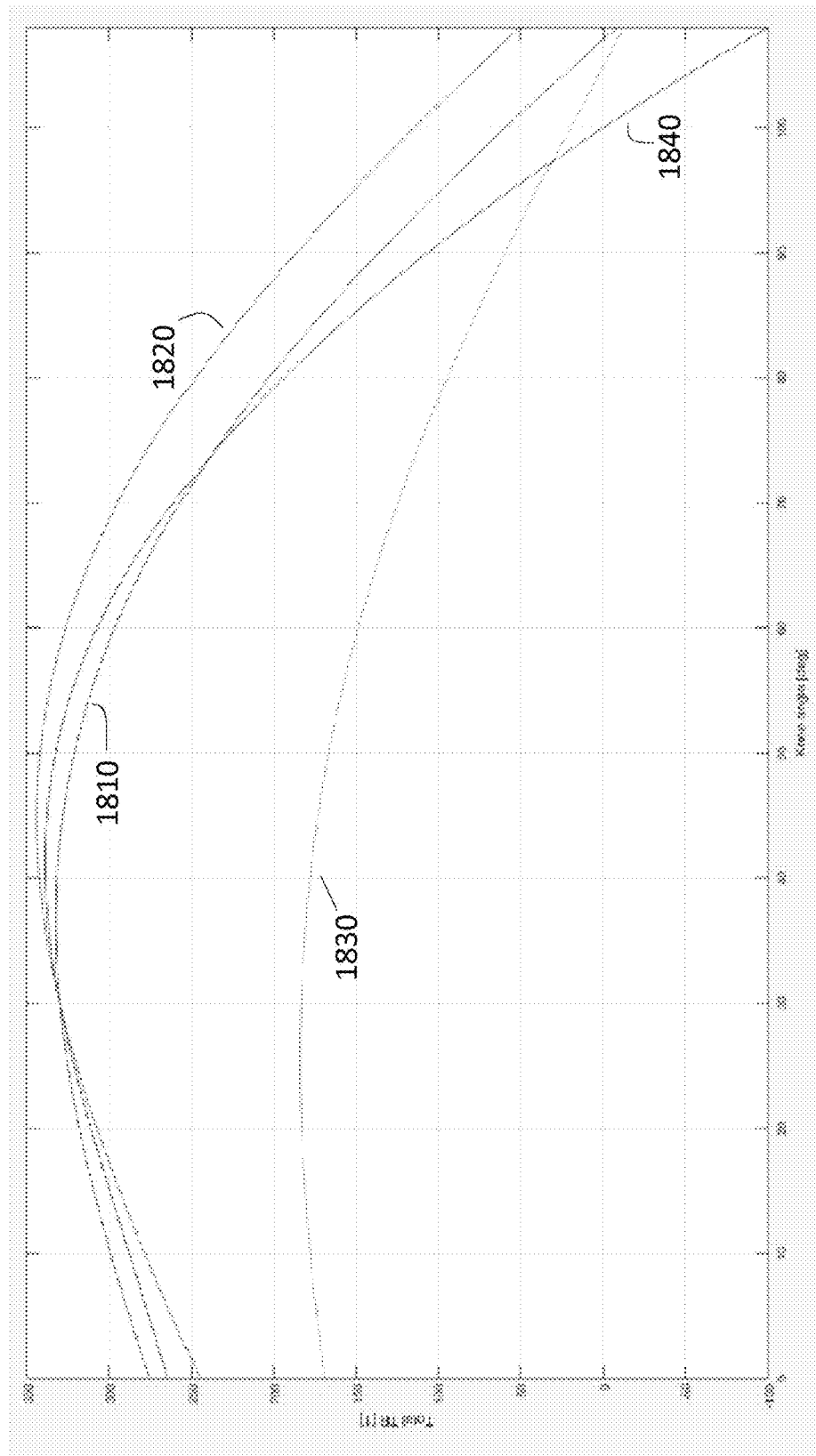
FIGS. 18A and 18B display plots of transmission ratio in various embodiments of an assistive device.

FIG. 18A displays a series of graphs plotting knee angle (x-axis) and total TR (y-axis). Negative TR means that (theoretically) the nut 1330 must be driven in the opposite direction, to continue angle extension. In the assistive device 1000, the point of zero-TR relates to the operation of the mechanical end stops.

Other locations for the linear actuator may be possible in alternative embodiments of the design for different applications. For example, the linear actuator 1300 may be located outside, in the front or in the back, with the motor 1310 pointing downward or upward, or with other spatial orientation depending upon the geometry of the synchronous transmission mechanism 1340. As shown in FIG. 15, the distance between the vertical axis of the knee joint 1030 and the axis parallel to the linear guidance 1260 passing through the rotational joint 1250 defines the offset e of the assistive device 1000. Additionally, setting the distance between the linear guidance 1260 and the lower part 1020 allows setting of the mechanism offset e, which can be matched with the transmission 1340 by choosing a belt 1370 of proper length.

Figure 18B:
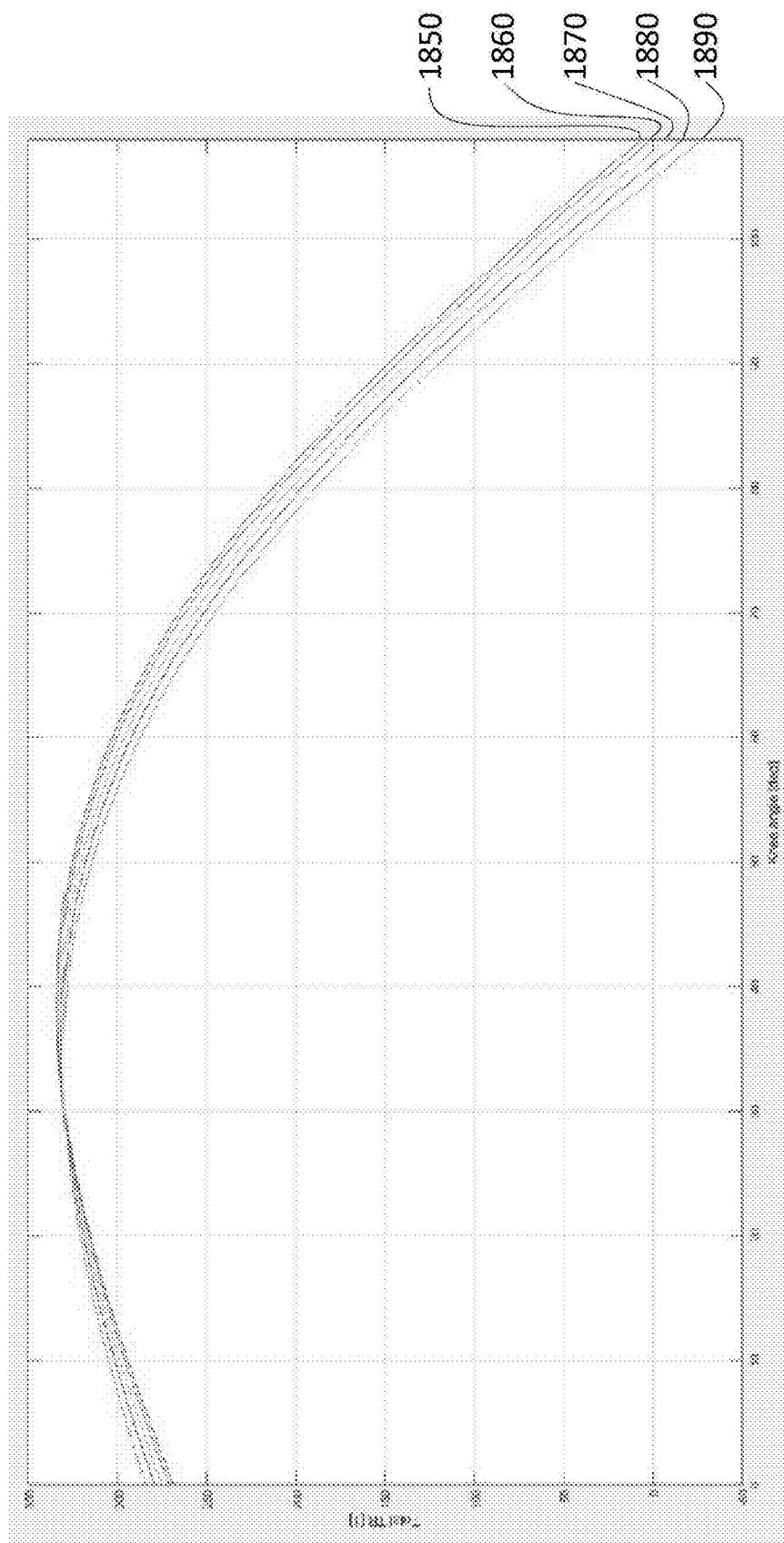
Figures 24A, 24B, 24C:
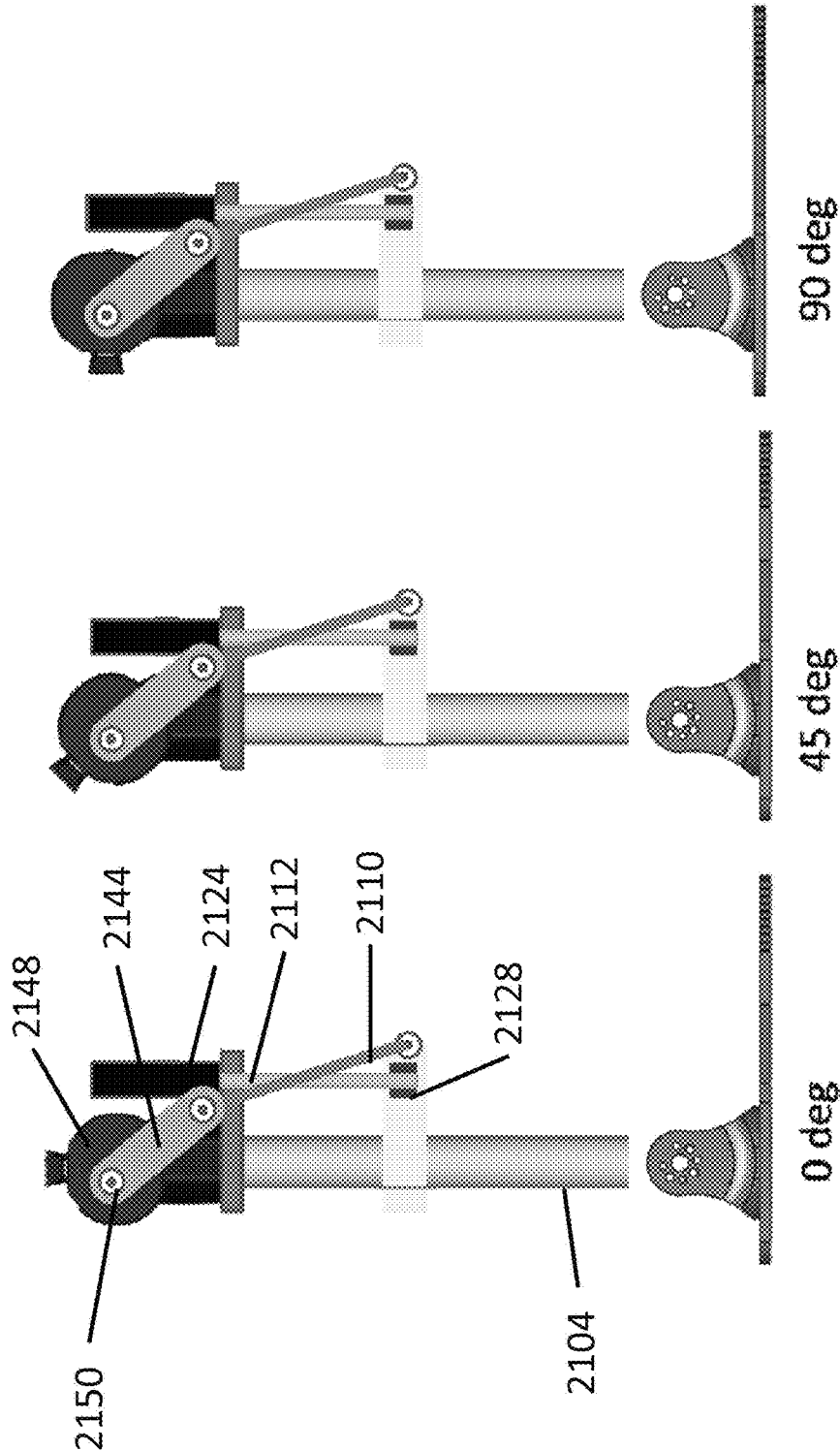
FIG. 24A displays a side view of an embodiment of an assistive device employing a revolute joint configuration at zero degrees.
FIG. 24B displays a side view of an embodiment of an assistive device employing a revolute joint configuration at 45 degrees.
FIG. 24C displays a side view of an embodiment of an assistive device employing a revolute joint configuration at ninety degrees.

In an embodiment, the dimensions may be adjusted such that e ranges in between 28.5 mm and 35 mm. More precisely, in an embodiment, the distance between the main vertical axis of the structure 1020 and the screw axis is 8 millimeters greater than the distance e. Alternately, the distance e may be characterized as 28.5 mm plus the gap between the lower part 1020 and the frame 1040 (see FIG. 5). This regulation is primarily for providing pretension to the belt 1370, as the correspondent variations in the TR curve are minimal. FIG. 18B displays plots of knee angle (x-axis) and transmission ration (y-axis) for exemplary values of e=38 (plot 1850), 35 (plot 1860), 32.5 (plot 1870), 30 (plot 1880) and 28.5 mm (plot 1890).

As shown in FIG. 13, the active component 1200 is positioned posterior to the pylon 2000, similar to the position of the gastrocnemius muscles relative to the shin of the human leg. In this position, and in other suitable positions, the active component 1200 and the rest of the assistive device 1000 may be covered, with a housing or other covering, such as a cosmetic covering. A covering may be made of one or more of a foam material, silicone, latex, rubber, vinyl, or other material known in the art. It may be rigid or flexible.

Figure 14A:
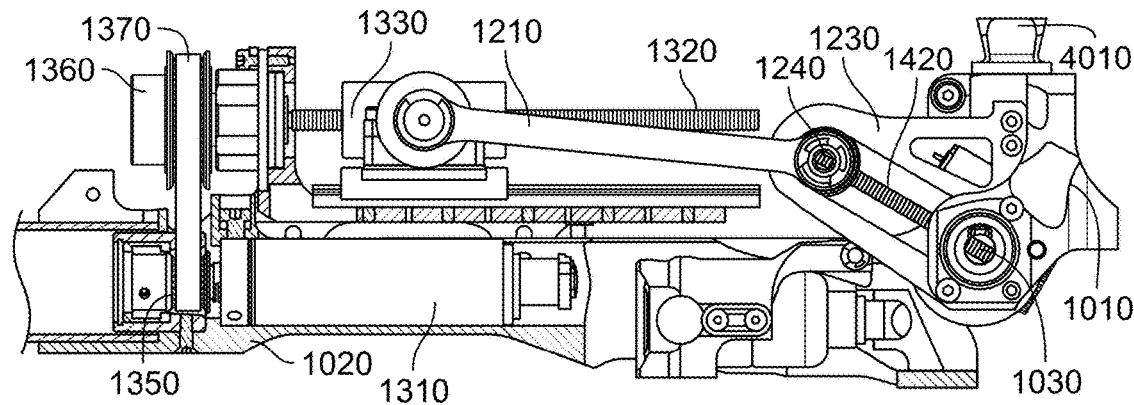
FIGS. 14A, 14B, and 14C each display, at various knee angles, a partial-sectioned view of an embodiment of an assistive device in a powered mode.
Figure 14B:
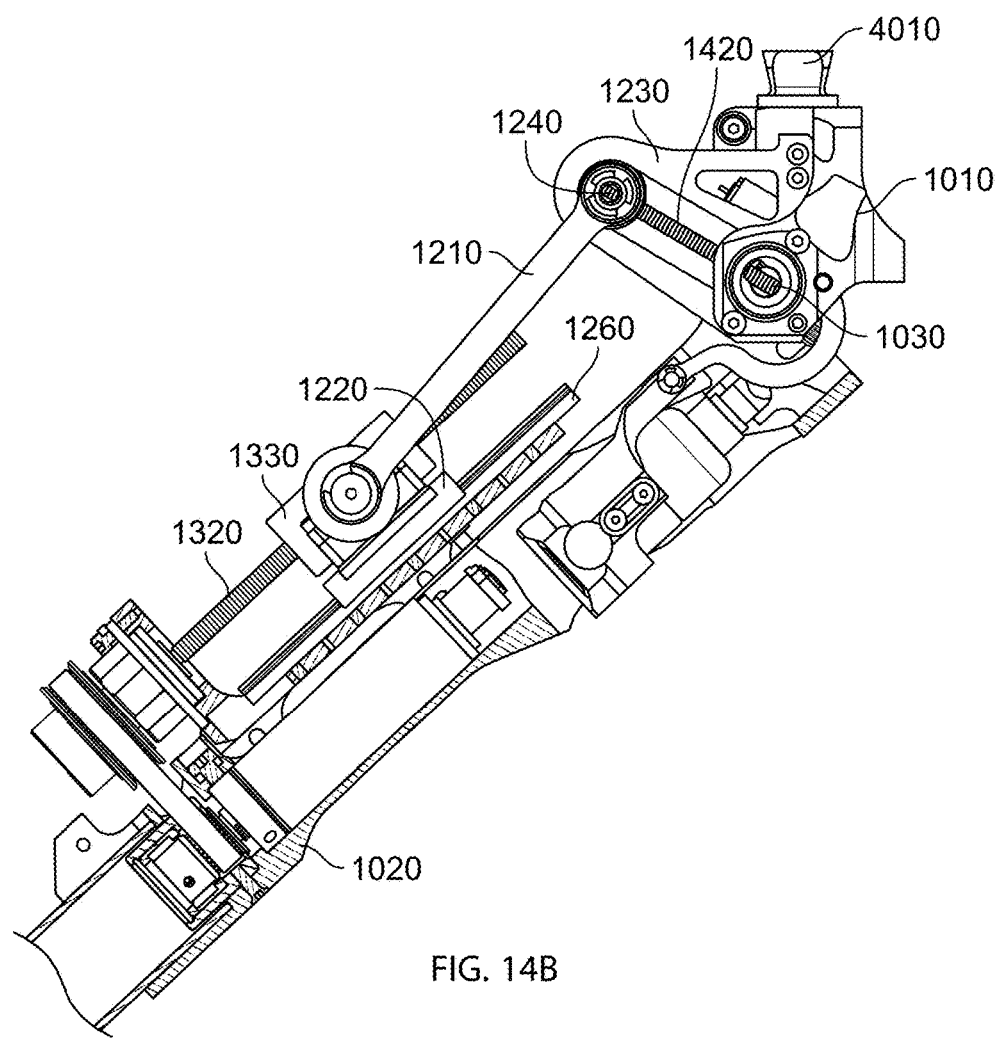
Figures 14C, 15:
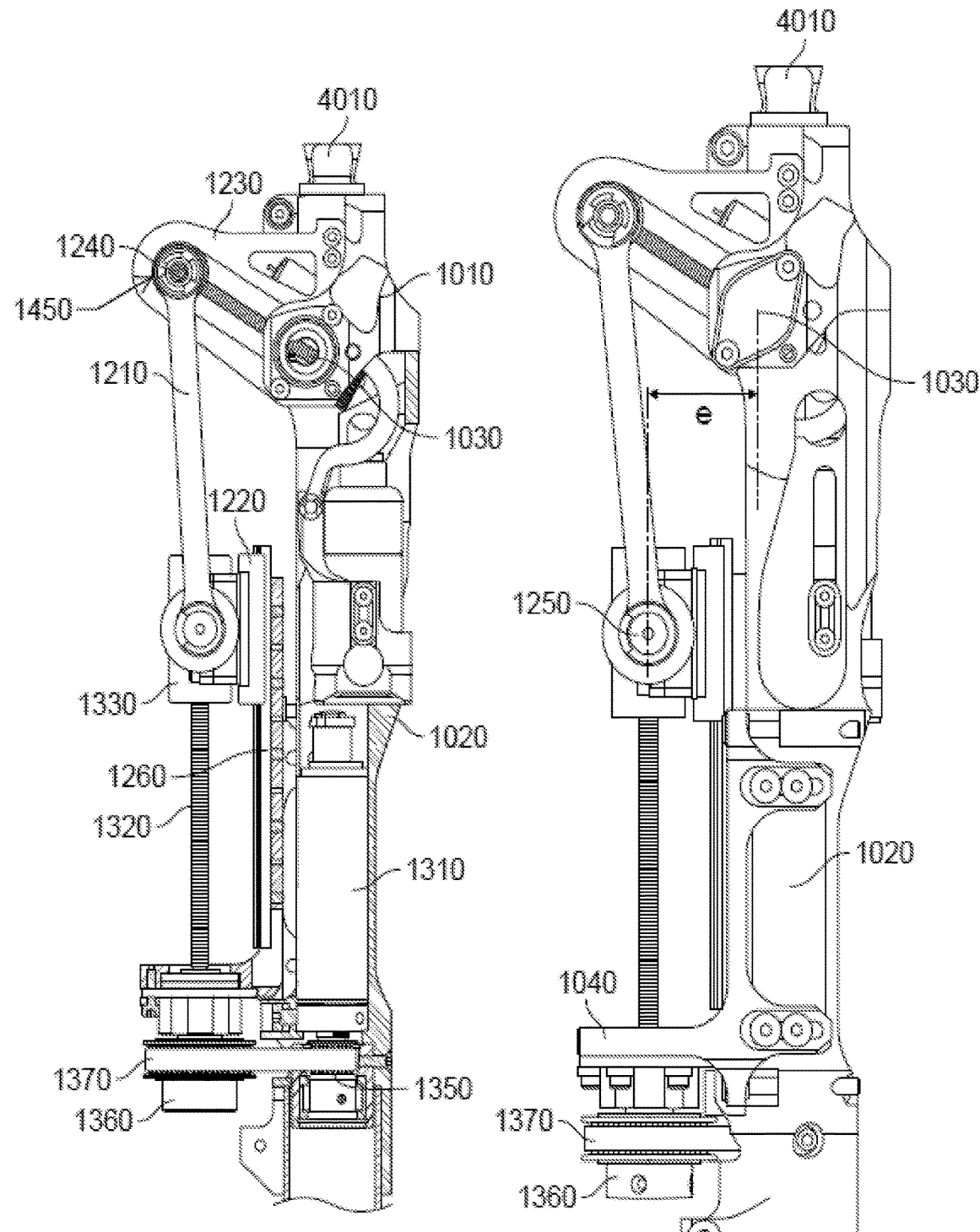
FIG. 15 displays an embodiment of an assistive device being acted upon by a pre-tensioning mechanism and the resulting slider-crank offset.

FIGS. 14A, 14B, and 14C display a side view of the assistive device 1000 at various stages of operation in powered mode. In FIG. 14, the nut 1330 begins at a position near to the distal end of the screw 1320. When the motor 1310 is turned on, its rotation causes the pulley 1350 to rotate, which pulls the belt 1370 so that it rotates around the pulley 1360. The pulley 1360 is mechanically coupled to the screw 1320, and so rotation of the pulley 1360 causes rotation of the screw 1320, which pulls the nut 1330 towards the proximal end of the screw 1320. Pulling of the nut 1330 in this proximal direction creates a pushing force on the connecting rod 1210, which transfers the pushing force to the crank 1230 through the rotational joint 1240. The rotational joint 1240 has a threaded interior that attaches to an adjustable linkage (e.g., a screw 1420) and prevents the force from the connecting rod 1210 from pushing the rotational joint 1240 proximally up the screw 1420. Instead, the force from the connecting rod 1210 pushes on the rotational joint 1240, which transfers the force to the crank 1230. The crank 1230 is rigidly affixed to the knee joint 1030, and so the force between the nut 1330 and the crank 1230 creates a torque that acts on the knee joint 1030, causing it to extend. FIG. 14B displays a side view of the assistive device 1000 with the knee joint bent at about a 45 degree angle. By comparing the position of the nut 1330 in FIG. 14A with the position of the nut 1330 in FIG. 14B, the reader can see how the change in position of the nut 1330 on the screw 1320 results in an extension of the knee joint 1030. As the nut 1330 continues moves proximally along the screw 1320, the knee joint 1030 more fully extends, as shown in FIG. 14C. The reader may compare the position of the nut 1330 in FIGS. 14A, 14B, and 14C to see how the change in attachment position of the nut 1330 on the screw 1320 causes extension of the knee joint 1030. Similarly, operating the motor 1310 in the reverse direction causes the screw 1320 to rotate in the opposite direction, which pulls the nut 1330 towards the distal end of the screw 1320, which creates a tension in the connecting rod 1210, the rotational joint 1240, and the crank 1230 that causes the knee joint 1030 to flex. The reader can see the change in the assistive device 1000 as the knee flexes by comparing FIG. 14C with FIG. 14B, and by comparing FIG. 14B with FIG. 14A.

For the assistive device 1000 to operate in passive mode, the motor 1310 and the linear actuator 1300 may be decoupled from a mechanism in the assistive device 1000 that assists in the rotation of the knee joint 1030. This can be done in several ways, including but not limited to disengaging the connection between the motor shaft 1310 and the screw 1320; disengaging the connection between the nut 1330 and the slider element 1220; disengaging the connection between the crank 1230 and the upper body 1010; or disengaging the connection between the sliding guidance 1260 and the lower part 1020. Decoupling the motor and/or linear actuator 1300 enables the knee joint 1030 to rotate independently of the rotation of the motor 1310 or actuation of the linear actuator 1300, so that a patient can walk (and so bend the knee joint 1030) without the use of the motor.

Alternatively, the decoupling of the motor and transmission from the knee joint may be achieved by selectively introducing an additional joint into the kinematic linkage between the motor 1310 and the knee joint 1030. As described above, this kinematic linkage includes the knee joint 1030, the crank 1230, the rotational joint 1240, the connecting rod 1210, the rotational joint 1250, and the slider 1220. Introducing an additional joint adds an extra degree of freedom in between the rotation of the motor 1310 and the rotation of the knee joint 1030. The rotation of the knee joint 1030 may be decoupled from the displacement of the nut 1330, and therefore from the movement of the linear actuator 1300 and the motor 1310. The additional joint may be coupled to a clutch, which can selectively engage or disengage the additional joint in order to transition the assistive device 1000 from powered mode to passive mode.

Figure 17A:
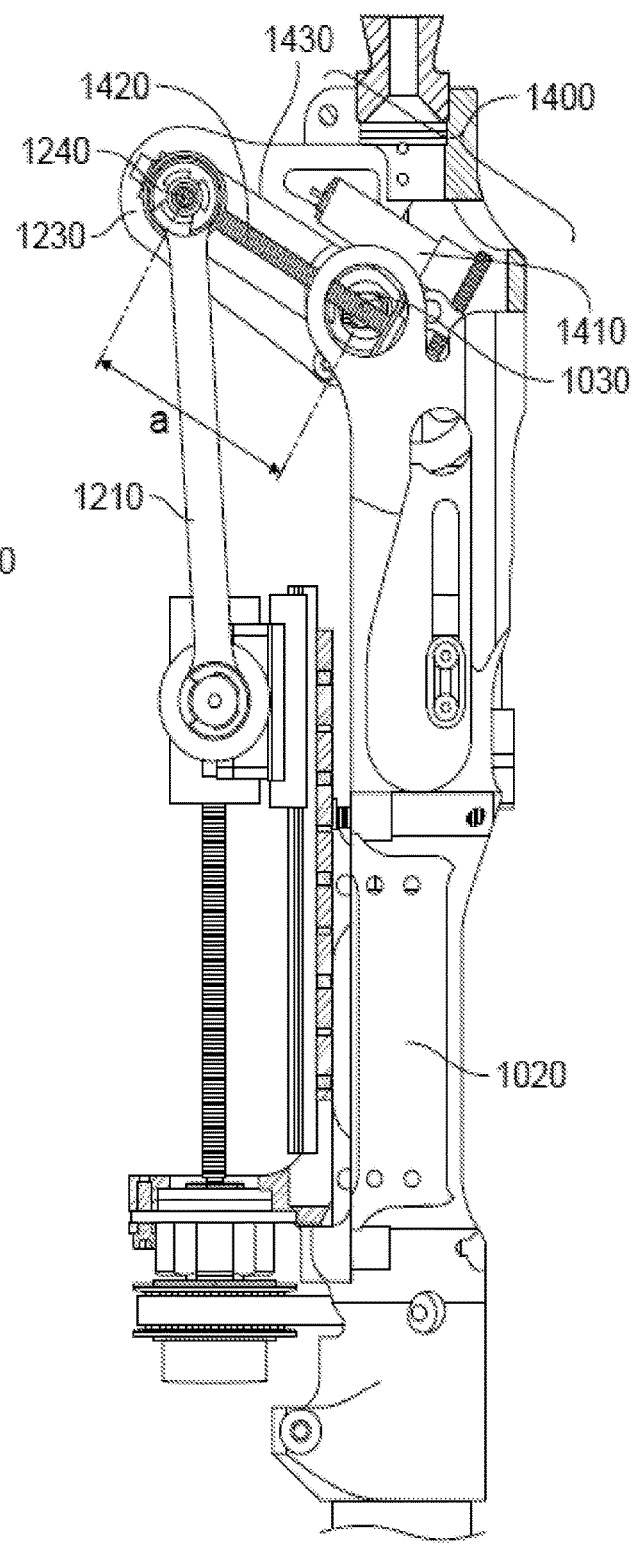
FIGS. 17A, 17B, and 17C each display a side view of an embodiment of an assistive device, indicating a transition between a powered mode and a passive move of the assistive device.
Figure 17B:
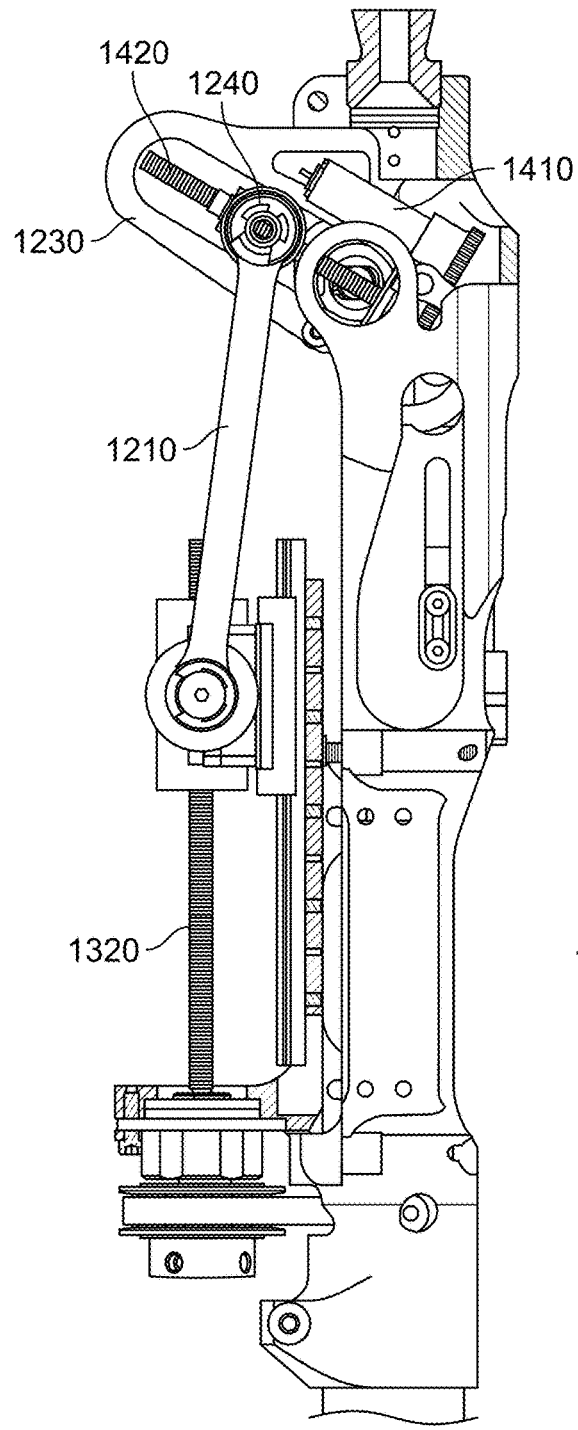
Figure 17C:
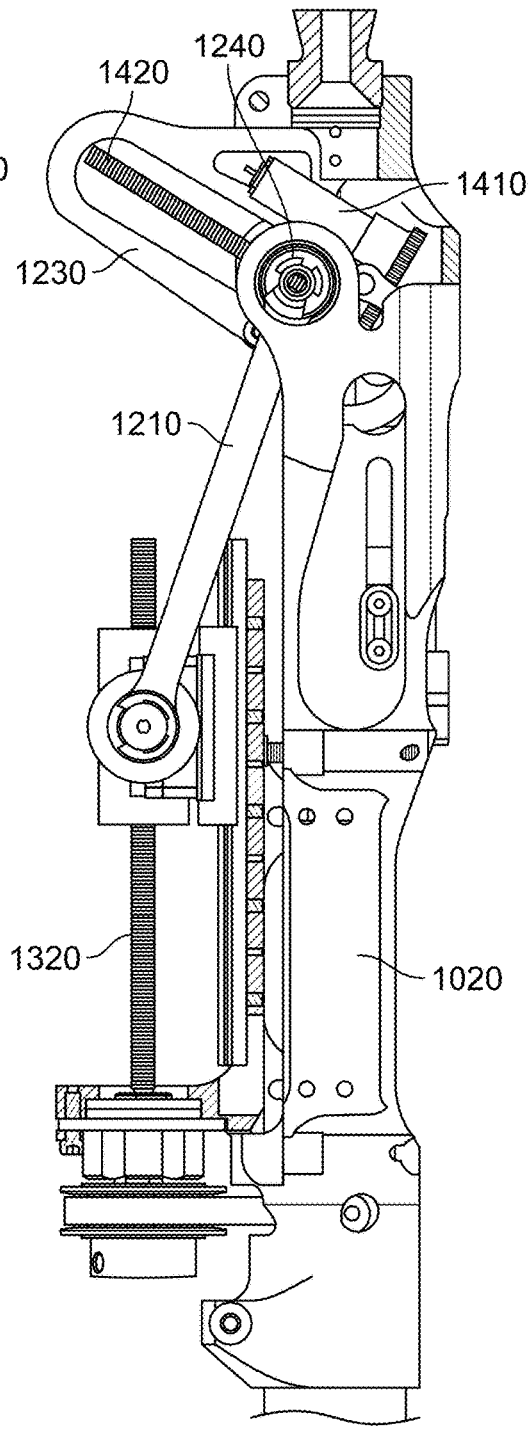

FIGS. 17A, 17B, and 17C each display a side view of an embodiment of the assistive device 1000 showing the assistive device 1000 transitioning from an powered mode (in FIG. 17A) to a passive mode (in FIG. 17C). In FIG. 17A, the rotational joint bar 1240 is positioned at the far end of a slot in the crank 1230. The rotational joint 1240 may be threaded and attached to the screw 1420. When the motor 1410 rotates the screw 1420, the rotational joint 1240 is moved along the length of the screw 1420. The sequence of FIGS. 17A, 17B, and 17C show the motor 1410 actuating to move the rotational joint 1240 from an end position (shown in FIG. 17A) to an intermediate position (shown in FIG. 17B) to a position that is coaxial to the knee joint (shown in FIG. 17C). The rotational joint 1240 may be positioned in other intermediate positions between the end position and the coaxial position. As the rotational joint 1240 moves towards the coaxial position, the moment arm a of the connecting rod 1210 acting on the knee joint 1030 reduces, until the rotational joint 1240 becomes coaxial with the knee joint 1030. When the rotational joint 1240 is coaxial with the knee joint 1030, the moment arm a has a length equal to 0, the active system becomes singular, and the patient is able to rotate the knee joint 1030 without a change in the position of the actuator 1300 and without requiring active motion or a torque from the linear actuator 1300.

Figure 16A:
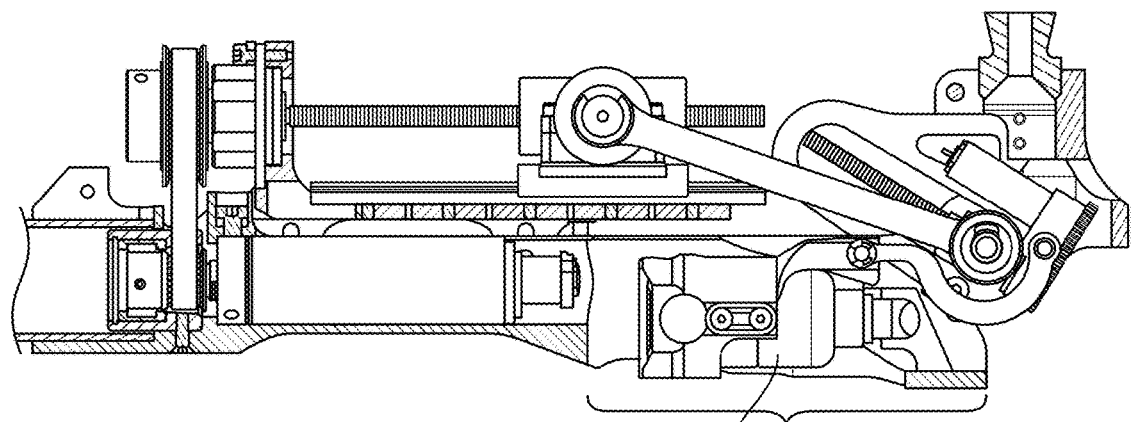
FIGS. 16A, 16B, and 16C each display, at various knee angles, a partial-sectioned view of an embodiment of an assistive device in a passive mode.
Figure 16B:
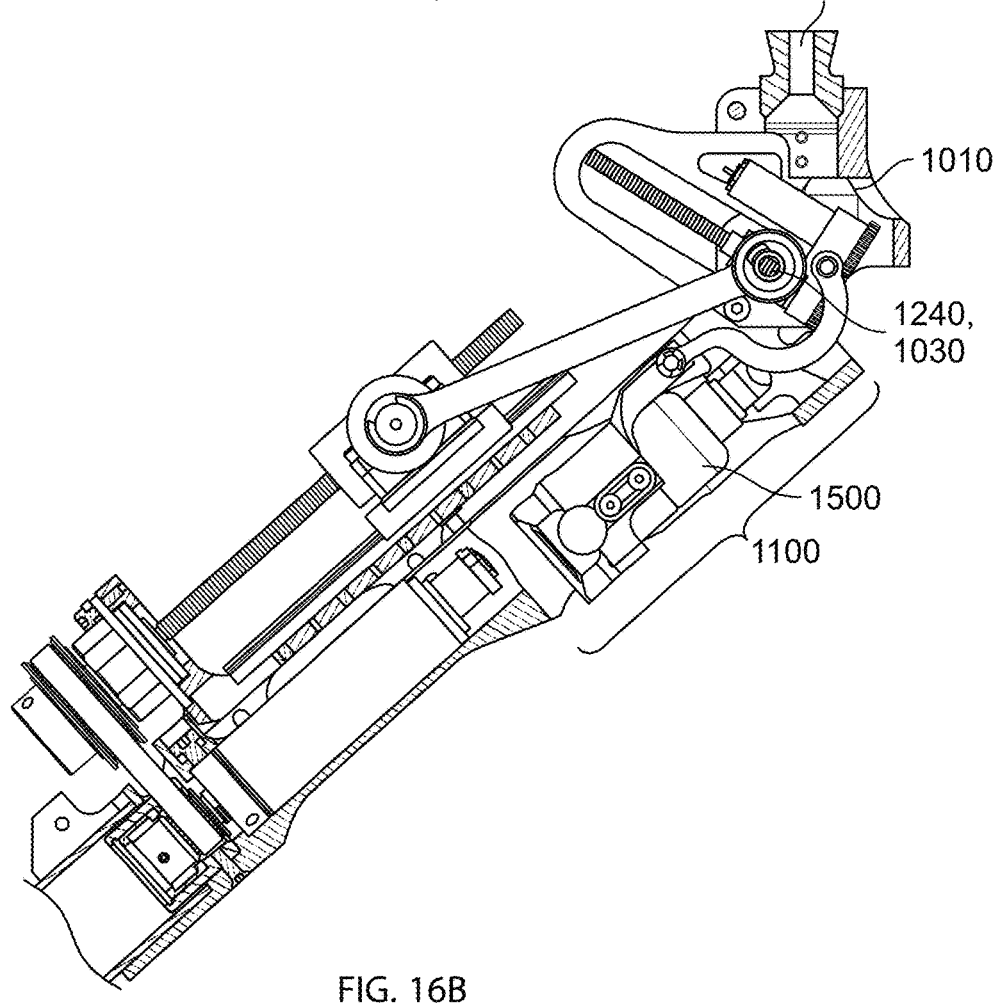
Figure 16C:
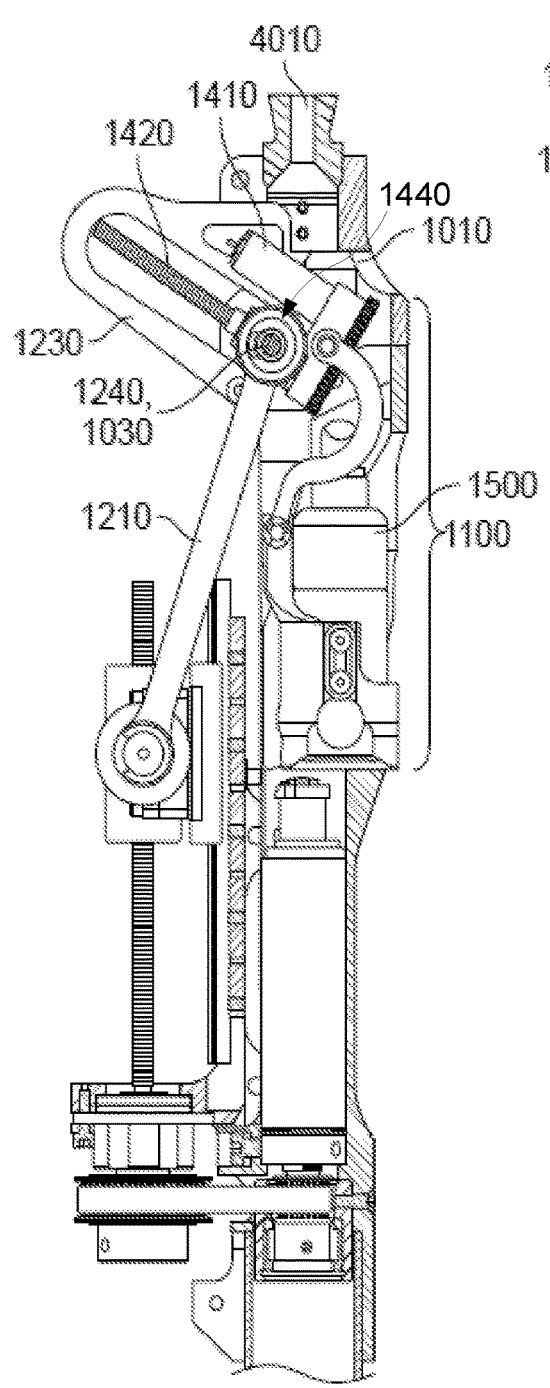

FIGS. 16A, 16B, and 16C each display a side view of the assistive device 1000 at various stages of operation in passive mode. FIG. 16C displays the assistive device 1000 in an upright position, as if the patient were standing on it. FIG. 16B displays the assistive device 1000 after the patient has taken a step forward with his or her sound leg, bringing the other leg (the assistive device 1000) into a swing phase and showing the assistive device 1000 swinging backwards. FIG. 16A shows the assistive device 1000 in a fully flexed position, which because it is so fully flexed would be rarely achieved by the patient during walking, and is shown here to help illustrate the general operation of the assistive device 1000 in a passive mode.

As shown in the FIGS. 16A, 16B, and 16C, the knee joint 1030 flexes but the active component (including the motor 1310, the transmission 1340, the linear actuator 1300, the nut 1330, the connecting rod 1210, the rotational joint 1240, and the screw 1420) are not in active movement. Although they rotate around the knee joint 1030 as the knee joint 1030 bends, they do not actuate and do not change position with respect to the position of the knee joint 1030 or the passive component 1100. The motion of the assistive device 1000 while in passive mode results from the energy the patient provides while operating the assistive device 1000 in a passive task. There are no other additional degrees of motion sliding, spinning or pivoting while the assistive device 1000 is passive, except for the rotation of the knee joint 1030 and the operation of the passive system 1100, such as the damper 1500. Limiting the duration of movement of the active components extends their life, increases battery life, reduces noise, allows for a lighter assistive device, and has other benefits.

The transition between the powered mode of the assistive device 1000 and the passive mode of assistive device 1000 may be provided by another small active system 1400. In an embodiment, the active system 1400 may comprise a small electrical motor 1410 driving a screw 1420, which drives the rotational joint 1240 along a slot 1430 (which may or may not be on a straight line) connecting the original position (at a distance a from the knee joint 1030) with the position of the knee joint 1030. The motor 1410 is activated only occasionally, during the transition between tasks, rather than continuously during the motion. Therefore, the motor 1410 can be driven at its maximum performances (for shorter transition time) without negative consequences on the thermal heating, electrical consumption, or mechanical life. Additionally, this allows the motor 1410 to be easily controlled at constant voltage, and switched off when the absorbed current overcomes a threshold that indicates the rotational joint 1240 has reached a mechanical stop in the slot of the crank 1230. This feature allows for control of the motor 1410 without the need for precise or resolute sensors, or additional control layers. In other embodiments, the screw 1420 and/or the motor 1410 may be replaced with or augmented by pneumatic, hydraulic, piezoelectric, or moving coil systems.

A minimal position sensor on the active system 1400 may be used to set the desired attachment position of the rotational joint 1240 along the screw 1420 and/or slot 1430 (e.g., any position(s) between a position 1440 in which the rotational joint 1240 is coaxial with the knee joint 1030 and an end position 1450), thus enabling the possibility to control the length a of the active mechanism 1200. This feature provides for an effectively tunable variable transmission. The additional advantage is the possibility to tune the contribution of the active mechanism, by lowering its torque transmission ratio with respect to the fully active configuration, but conversely increasing its speed ratio, basically without affecting the performances of the motor 1310. This feature is advantageous as it allows to meet requirements for mildly-power and varying-speed tasks (e.g. raising a slope, fast walking). The assistive device 1000 may be controlled using a microcontroller which receives information from sensors coupled to the assistive device 1000, such as encoders, load cells, IMUS, and the like which, for instance, help determine the position of the knee joint 1030. The microcontroller may output a needed amount of current to a first current driver, used to control the motor 1310, and a second current driver, used to control the motor 1410. Each current driver and motor combination may employ a closed feedback loop. One skilled in the art will recognize that there are many other ways to configure the electronics to control the assistive device.

In an embodiment, a method for operating the assistive device 1000 is described as follows. The controller of the assistive device 1000 receives a first set of information from sensors coupled to the assistive device 1000. The first set of information indicates that the assistive device 1000 will operate in a powered task, such as climbing stairs. The motor 1410 moves the rotational joint 1240 to the appropriate location along the screw 1420, for instance, the position furthest from the knee 1030, and the motor 1310 begins to actuate. Actuation of the motor 1310 causes the nut 1330 to travel away from the knee joint 1030, drawing the lower part including the pylon 2000 up and causing the knee 1030 to flex in preparation for climbing a stair. The assistive device continues to operate to provide the necessary flexion and extension to assist the user up the staircase. At the top of the stairs, the controller receives a second set of information from the sensors coupled to the assistive device 1000. The second set of information indicates that the assistive device will transition to a passive task, such as level ground walking. The motor 1410 moves the rotational joint 1240 inwardly towards the knee 1030 until the rotational joint 1240 is coaxial to the knee 1030. The motor 1310 and the linear actuator 1300 stop actuating. The user is able to walk along level ground, with the damper 1500 providing the appropriate passive resistance, and without requiring actuation of the active components such as the motor 1310, the linear actuator 1300, the rod 1210, and the rotational joint 1240. Similar methods may be employed to transition the assistive device between other powered tasks and passive tasks.

Various other embodiments of assistive devices that employ principles similar to those described above are displayed in FIGS. 19-27. Starting with FIG. 19, an assistive device 2100 comprises a knee joint 2102 that has both passive and active components, and a pylon 2104 that connects the knee joint 2102 to the foot component 2106. In one embodiment the active component of the knee joint 2102 is actuated through a four-bar linkage in an offset slider crank configuration. In this configuration, the knee angle is defined by the crank angle plus an angular offset that can be set by design to optimize the range of motion and torque/speed capability of the offset slider crank mechanism for specific device applications. A connecting link 2110 transmits the movement between the slider 2112 (which in one embodiment may be screw 2126), which is located in parallel to the pylon, and the crank 2114. The connecting link 2110 attaches to the crank 2114 with a rotational joint 2116. The connecting link 2110 also attaches to a slider 2112 with a rotational joint 2118. The distance between the location of rotating knee joint 2120 and rotational joint 2118 in the x axis defines the offset of the mechanism. The slider 2112 is connected to a linear actuator, which in one embodiment comprises a DC motor 2124, a screw 2126 (which in various embodiments may be a ball screw, lead screw, or roller screw) and a screw nut 2128. The shaft of motor 2124 is attached to the screw 2126, so that one rotation of the motor shaft equals one rotation of the screw. The nut 2128 is driven up/down on the screw 2126 by rotation of the motor shaft. The nut 2128 is connected to the rotational joint 2118 with a supporting link 2130. The supporting link 2130 connects to the pylon 2104 through linear bearings, which in various embodiments may be ball bearings or plastic bearings, that allow the supporting link 2130 to slide freely up-down on the pylon 2104 (as shown in one embodiment in FIGS. 20A, 20B, and 20C) without rotating with respect to said pylon 2104. Therefore, in one embodiment, the supporting link 2130 allows the slider to move and also allows the motor 2124 to drive the slider 2112.

In various embodiments, the linear actuator can be located in different positions (FIG. 21). For example, it can be located outside the pylon in the front, outside the pylon in the back, or inside the pylon. Other locations for the linear actuator may be possible in alternative embodiments of the design for different applications.

For the assistive device 2100 to operate in passive mode, the motor 2124 and the powered linear transmission 2132 may be decoupled from knee rotation. This enables the knee joint to rotate independently of the motor 2124 and transmission 2132. The decoupling of the motor and transmission from the knee joint can be achieved in one embodiment by selectively introducing an additional joint to the kinematic chain (which in the embodiment previously described comprises three rotational joints 2120, 2116, 2118; the slider 2112; and links 2114 and 2110) for the powered mode operation. This additional joint adds an extra degree of freedom in between the motor rotation and the knee joint rotation, which allows decoupling the rotation of the knee joint 2102 from the displacement of the nut 2128, and therefore from the rotation of the transmission and the motor 2124.

The additional joint can be added at several locations in the kinematic chain comprising the offset slider-crank. In various embodiments, the additional joint may be a prismatic joint or a revolute joint, or other suitable joint.

In one embodiment (FIG. 22), a prismatic joint is added by disconnecting the nut 2128 from the supporting link 2130 so that the position of rotating joint 2118 becomes independent of the position of nut 2128. In this kinematic configuration, when the knee joint 2102 rotates, the connecting link 2110 causes the supporting link 2130 to slide along the pylon 2104 without causing the nut 2128 to move, and therefore without requiring rotation of the motor 2124.

In one embodiment (FIG. 23), the nut 2128 is selectively disconnected from the supporting link 2130 using an asymmetric mechanism that uses a fixed mechanical end-stop 2140 on one side and a movable end-stop 2142 on the other. This switching mechanism allows movement of the nut 2128 with respect to the supporting link 2130 to be locked as needed to transition between active and passive modes. The fixed mechanical end-stop 2140 prevents the nut 2128 from moving upward with respect to the supporting link 2130. Guides 2125 prevent rotation of the nut 2128 with respect to the supporting link 2130 as a result of rotation of screw 2126. The action of the fixed mechanical end-stop 2140 depends on the relative position of the motor shaft 2125 and the knee joint 2102. For any knee joint position, there is a motor shaft position that causes the nut to contact the fixed mechanical end-stop 2142 on the supporting link 2130. Therefore, the motor 2124, which moves the knee joint 2102 in powered mode, can also lock knee joint movement in one direction without the intervention of any other mechanism.

Locking the knee joint 2102 in the opposite direction (i.e., nut moving downward) requires a movable linkage to constrain the added prismatic joint. In one embodiment (FIG. 23, side view), the movable linkage can be composed of one or two links 2142 that rotate or displace in the horizontal plane until their moving ends enter into a slot 2141, which may be machined into the supporting link 2130. The slot 2141 provides support for the vertical interaction forces between the nut 2128 and the supporting linkage 2130 as required to lock the additional prismatic joint, and to set the knee joint 2102 in powered mode.

In another embodiment (FIG. 24), transitions between passive and powered modes may be achieved by adding a revolute joint in between the crank link 2146 and the knee link 2148, concentric to the rotating knee joint 2150. This additional degree of freedom allows the knee joint 2102 to rotate independently with respect to the crank link 2146. As a consequence, the knee joint 2102 also moves independently with respect to all the linkages of the slider-crank mechanism, and no movement is transmitted to the nut 2128, the screw 2126, or the motor 2124.

Switching between the passive and powered mode requires selective locking/unlocking of the additional revolute joint. In one embodiment, this is can be achieved by using a fixed (immobile) mechanical end-stop 2150 built as part of the knee joint 2102, and a moveable pin 2154. The mechanical end-stop 2150 and the movable pin 2154 lock the rotation of the crank link 2146 with respect to the knee link 2148. Thus they can selectively introduce or remove an additional degree of freedom in the kinematic chain.

In another embodiment, the additional revolute joint may be locked by using a pawl-ratchet mechanism (FIG. 26). The ratchet 2156 is fixed to the crank link 2146. The pawl 2158 is attached to, and rotates with respect to pylon 2104 through a revolute joint. As it rotates, the pawl 2158 contacts the ratchet 2156, which locks it in position.

In yet another embodiment, an additional degree of freedom can be selectively introduced or removed from the kinematic chain by using a singularity (FIG. 27). In this embodiment the crank link 2146 and the knee link 2148 are connected through an additional revolute joint 2160. The revolute joint 2160 is located half-way in between the knee joint 2150 and the revolute joint 2116 that attaches the crank link 2146 to the connecting link 2110, such that the distance from revolute joint 2150 to revolute joint 2160 equals the distance from revolute joint 2160 and revolute joint 2118.

When revolute joint 2160 is locked, the assistive device is in powered mode (the knee kinematics is an offset slider crank mechanism). When revolute joint 2160 is unlocked, the crank link 2146 can rotate with respect to revolute joint 2160 and fold on the knee link 2148 so that rotating joint 2150 and revolute joint 2116 align. The rotation of the crank link 2146 can be generated by the motor 2124 moving the nut 2128 and the connecting link 2110. The folding of the crank link 2146 and the consequent alignment of revolute joint 2116 on rotating joint 2150 causes a degeneration of the kinematic chain (singularity). Due to this kinematic degeneration, the knee link 2148 can rotate without causing the displacement of the connecting link 2110. Therefore, in this "folded" configuration, the knee joint 2102 can rotate independently with respect to the motor 2124. In this embodiment, not only the motor 2124 and transmission but also the crank link 2146, the slider 2112, and the connecting link 2110 do not move in the passive mode.

Figure 28:
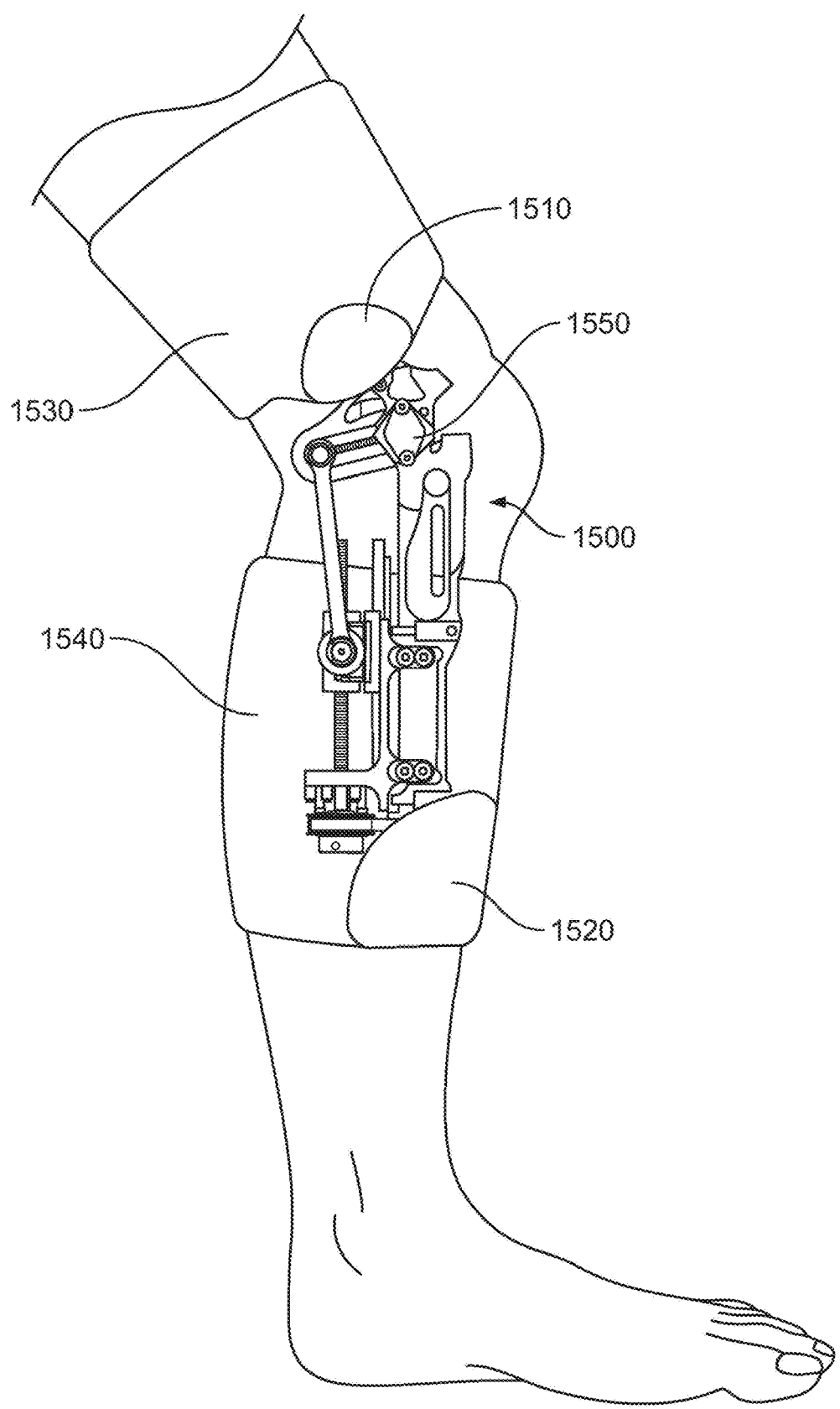
FIG. 28 displays a side view of an embodiment of an orthosis.

In another embodiment, an assistive device may comprise an orthosis. For example, the orthosis 1500 may be a hybrid powered orthosis for motion assistance. In one embodiment, shown in FIG. 28, the orthosis 1500 may have components similar to the assistive device 1000 shown in FIG. 3. The orthosis 1500 may be arranged in parallel to a patient's lower limb, with upper and lower parts 1510 and 1520 interacting one with the user's thigh and the other with the shank (to which anatomical segment where to attach the most cumbersome part 1520 can be chosen basing on the specific addressed user), and with the axis of the joint 1550 substantially aligned with the user's knee joint. Braces 1530 and 1540 may connect the orthosis 1500 to the patient's limb. In such configuration, using the same principles described above, the orthosis 1500 may be used an active power source for motion assistance, or as a passive orthosis. Additionally, in other embodiments, the system may be employed on an exoskeleton, resulting in an exoskeleton with smaller motors and batteries than those employed in always active powered exoskeletons. Conversely, when in passive mode the system will behave as a passive orthosis for enhanced stability. It should be understood that the orthosis 1500 shown in FIG. 28 is only one of many different types of orthoses that may utilize the basic principles described herein. Additionally, as a generalization, the same principles may be used by one of ordinary skill in the art to develop other wearable powered orthoses, for assistance orthoses at different anatomical joints like the hip joint (with a brace at the trunk and another brace at the thigh, the joint of the orthosis aligned with the hip flexion/extension axis), the ankle joint (with a brace at the shank and another brace at the foot, the joint of the orthosis aligned with the ankle dorsi/plantar flexion axis), or an upper-limb joint, such as the elbow joint.

Although the described embodiments of the assistive device and their advantages have been described in detail, a person of ordinary skill in the art would understand that various changes, substitutions, and alterations can be made without departing from the spirit and scope of the claimed subject matter as defined by the appended claims.

What is claimed is:

1. An assistive device for replacing or augmenting a limb of an individual, comprising
    a knee joint for connecting an upper and a lower part of the assistive device, the knee joint having an axis of rotation,
    a crank member having a first and a second end and operably coupled to the knee joint and an actuator linkage,
    the actuator linkage having a link portion including a rotational joint that is movable between a first position at the first end of the crank member where the rotational joint is coaxial with the axis of rotation of the knee joint and a second position at the second end of the crank member where the rotational joint is located at a distance from the knee joint,
    wherein in the first position, the assistive device may operate in a passive mode such that the actuator linkage does not provide torque to the knee joint, and in the second position, the assistive device may operate in a powered mode such that the actuator linkage is capable of applying a torque to the knee joint.

2. The assistive device of claim 1, wherein the actuator linkage applies the torque to the knee joint about the rotational joint.

3. The assistive device of claim 1, further comprising an adjustable linkage extending from the knee joint to a predetermined end position; the rotational joint being movable along the adjustable linkage between the first position and the second position.

4. The assistive device of claim 3, wherein the adjustable linkage comprises a screw.

5. The assistive device of claim 1, the actuator linkage further comprising a linear actuator.

6. The assistive device of claim 5, the knee joint being able to move to a flexed position without actuation of the linear actuator when the rotational joint is in the first passive mode position.

7. The assistive device of claim 5, the knee joint being extendable without actuation of the linear actuator when the rotational joint is in the first passive mode position.

8. The assistive device of claim 5, the knee joint being able to move to a flexed position and to an extended position without actuation of the linear actuator when the link portion is in the first passive mode position.

9. The assistive device of claim 5, wherein the linear actuator comprises a connecting rod, the connecting rod is provided at one end with the rotational joint and is movable with the rotational joint along the crank member between the first and second positions.

10. The assistive device of claim 5 wherein the actuator linkage further comprises a connecting rod coupled to the linear actuator, the connecting rod transmitting motion from the linear actuator to the rotational joint.

11. The assistive device of claim 5, further comprising a motor for actuating the linear actuator, the linear actuator being positioned so that an actuating axis of the linear actuator is parallel to but not coaxial with an axis of the motor.

12. The assistive device of claim 11, wherein an outer face of the motor is in contact with a portion of the assistive device to dissipate heat generated by the motor.

13. The assistive device of claim 11 further comprising a transmission mechanism operatively coupled to the motor and to the linear actuator for applying driving power from the motor to the linear actuator.

14. The assistive device of claim 11 wherein the motor and the linear actuator are decoupled from the knee joint in the passive mode.

15. The assistive device of claim 1, wherein the second powered mode position is a predetermined position.

16. The assistive device of claim 15, wherein the rotational joint is movable to an intermediate position between the first position and the second position.

17. The assistive device of claim 1, wherein the actuator linkage further comprises a screw, a nut, and a connecting rod.

18. The assistive device of claim 1 further including sensors for collecting information for switching between the powered mode and the passive mode.

19. The assistive device of claim 1 further including a user switch in operative communication with the device for switching between the powered mode and the passive mode.

* * * * *